(12) United States Patent
Marsh et al.

(10) Patent No.: US 11,768,167 B2
(45) Date of Patent: Sep. 26, 2023

(54) FERROCENE LABELS FOR ELECTROCHEMICAL ASSAY AND THEIR USE IN ANALYTICAL METHODS

(71) Applicant: Binx Health Limited, Trowbridge (GB)

(72) Inventors: Barrie Marsh, Trowbridge (GB); Jonathan Sharp, Bath And Northeast Somerset (GB); Stephen Flower, Melksham (GB); Christopher Frost, Bath And Northeast Somerset (GB)

(*) Notice: Subject to any disclaimer, the term of this patent is extended or adjusted under 35 U.S.C. 154(b) by 248 days.

(21) Appl. No.: 17/094,473

(22) Filed: Nov. 10, 2020

(65) Prior Publication Data

US 2021/0116409 A1    Apr. 22, 2021

Related U.S. Application Data

(60) Division of application No. 16/666,750, filed on Oct. 29, 2019, now Pat. No. 10,830,728, which is a continuation of application No. 15/908,133, filed on Feb. 28, 2018, now Pat. No. 10,495,600, which is a continuation of application No. 13/996,748, filed as application No. PCT/GB2011/052573 on Dec. 22, 2011, now abandoned.

(30) Foreign Application Priority Data

Dec. 22, 2010 (GB) .................................. 1021896

(51) Int. Cl.
| | | |
|---|---|---|
| *G01N 27/327* | (2006.01) | |
| *C07F 17/02* | (2006.01) | |
| *C12Q 1/6816* | (2018.01) | |

(52) U.S. Cl.
CPC ......... *G01N 27/3276* (2013.01); *C07F 17/02* (2013.01); *C12Q 1/6816* (2013.01)

(58) Field of Classification Search
CPC . C07F 17/02; C12Q 1/6816; C12Q 2563/113; G01N 27/3276
See application file for complete search history.

(56) References Cited

U.S. PATENT DOCUMENTS

| | | | |
|---|---|---|---|
| 7,803,572 | B2 | 9/2010 | Braven et al. |
| 9,127,308 | B2 | 9/2015 | Braven et al. |
| 10,094,800 | B2 * | 10/2018 | Braven ............... G01N 27/308 |
| 10,495,600 | B2 | 12/2019 | Marsh et al. |
| 10,830,728 | B2 * | 11/2020 | Marsh ................ C12Q 1/6816 |
| 2005/0221315 | A1 | 10/2005 | Braven et al. |
| 2015/0159203 | A1 | 6/2015 | Braven et al. |
| 2015/0293107 | A1 | 10/2015 | Marsh et al. |
| 2016/0025703 | A1 | 1/2016 | Braven et al. |
| 2016/0244815 | A1 | 8/2016 | Marsh et al. |

FOREIGN PATENT DOCUMENTS

| | | |
|---|---|---|
| CN | 101189521 A | 5/2008 |
| JP | 2003125798 A | 5/2003 |
| JP | 2006098342 A | 4/2006 |
| JP | 2006325477 A | 12/2006 |
| WO | 03074731 A2 | 9/2003 |
| WO | 2005005657 A1 | 1/2005 |

OTHER PUBLICATIONS

Alvarez, 2001, Modulation of the Electronic Communication Between Two Equivalent Ferrocene Centers by Proton Transfer, Solvent Effects and Structural Modifications, Journal of Supramolecular Chemistry 1, pp. 7-16.
Alvarez, 1999, Structural and pH Control of the Electronic Commumnication between Two Identical Ferrocene Sites, Organometallics, 18:5733-5734.
Baldoli, 2006, A new triferrocenyl-tris(hydroxymethyl)aminomethane derivative as a highly sensitive electrochemical marker of biomolecules: Application to the labeling of PNA monomers and their electrochemical characterization, Chemisrty—A European Journal, 12(15):4091-4100.
Beer, 1998, Tunable bis(ferrocenyl) receptors for the solution-phase electrochemical sensing of transition-metal cations, J. Chem. Soc., Dalton Trans., pp. 417-423.
Biot, 2006, Probing the Role of the Covalent Linkage of Ferrocene into a Chloroquine Template, J. Med. Chem., vol. 49, pp. 4707-4714.
International Search Report and Written Opinion issued in International Application No. PCT/GB2011/052573, dated Mar. 9, 2012, 9 pages.
Kerr, 2000, Synthesis and Structure of N-ferrocenylglycosylamines; redox chemistry of O-ferrocenylglycosides and N-ferrocenylglycosylamines, J. Chem. Soc., Dalton Trans., pp. 1411-1417.
Kühnert, 2008, Phosphinoferrocenyl-terminated amidoamines: Synthesis and catalytic utilization in palladium-mediated C—C bond forming reactions, Journal of Molecular Catalysis A: Chemical 285, pp. 41-47.

(Continued)

*Primary Examiner* — Galina M. Yakovleva
(74) *Attorney, Agent, or Firm* — Withers Bergman LLP; Thomas C. Meyers

(57) ABSTRACT

Compounds of general formula I are used as labels in an electrochemical assay: (I) in which: Fc and Fc' are substituted or unsubstituted ferrocenyl moieties, X is a C1 to C6 alkylene chain which is optionally interrupted by —O— or —NH—; Y is a C1 to C6 alkylene chain which is optionally interrupted by —O— or —NH—; Z is a C1 to C12 alkylene chain which may optionally be substituted and/or may optionally be interrupted by —O—, —S—, cycloalkyl, —CO—, —CONR1-, —NR1CO— or —NR1- in which R1 represents hydrogen or C1 to C4 alkyl; and R is a linker group. Compounds I are used to make labelled substrates, as well as functionalised compounds for making the labelled substrates.

2 Claims, 9 Drawing Sheets

(56) References Cited

OTHER PUBLICATIONS

Sato, 2005, Electrochemical detection of telomeric quadruplex DNA using ferrocenyl naphthalene diimide, Nucleic Acids Symposium Series, 49:237-238.

STN Columbus Database entry. Ferrocene, 1,1—[[(carboxymethyl)imino]bis(methylene)]bis-(9Cl), entered Oct. 22, 2004.

Vilaplana, 2002, Synthesis of the novel chiral 1, 3-amino alchol 8-N, N-bis(ferrocenylmethyl)amino-menthol and its use as catalyst in the enantioselective addition of diethylzinc to aldehydes, Tetrahedrom: Asymmetry, 13(1):5-8.

* cited by examiner

FERROCENE LABELS FOR ELECTROCHEMICAL ASSAY AND THEIR USE IN ANALYTICAL METHODS

CROSS-REFERENCE TO RELATED APPLICATIONS

This application is a divisional of U.S. patent application Ser. No. 16/666,750, filed Oct. 29, 2019, which is a continuation of U.S. patent application Ser. No. 15/908,133, filed on Feb. 28, 2018, which is a continuation of U.S. patent application Ser. No. 13/996,748 entitled "Novel Ferrocene Labels for Electrochemical Assay and their Use in Analytical Methods," filed on Oct. 31, 2013, which is a national stage application, filed under 35 U.S.C. § 371, of International Application No. PCT/GB2011/052573, filed on Dec. 22, 2011, and claims the benefit of, and priority to, GB Patent Application No. 1021896.4, filed on Dec. 22, 2010, the complete contents of which are hereby incorporated herein by reference in their entirety for all purposes.

FIELD OF THE INVENTION

The invention relates to electrochemical detection methods. More especially, the invention relates to electrochemical assays, to electrochemically active labels for use in electrochemical detection methods, and to their use.

BACKGROUND OF THE INVENTION

The detection of certain biological molecules plays an important part in many aspects of life. For example, in the medical field, there is an ever-present need to detect bacterial or viral pathogens, or biological molecules. Other fields in which sensitive assays are essential include the food and beverage industries.

WO 03/074731 discloses a method of probing for a nucleic acid. A nucleic acid solution is contacted with an oligonucleotide probe with an electrochemically active marker. The probe is caused to at least partially hybridise with any complementary target sequence which may be present in the nucleic acid solution. Following enzymatic degradation of the nucleic acid probe, 30 information is electrochemically determined relating to the marker. Compounds for use in the method are also disclosed.

WO02005/05657 discloses a method of detecting protease activity in which a sample solution is contacted with a protease substrate with an electrochemically active marker, providing conditions under which any protease which may be present in the sample may degrade the protease substrate and information relating to the electrochemically active marker is electrochemically determined. Certain novel compounds for use in the process were also disclosed.

There is a continuing need to develop labels that enable detection of the presence in small concentrations of biological substrates or indicators, for example, nucleic acids (in isolated form or in the form of larger molecules, for example, natural or synthetic oligonucleotides), or amino acids (in isolated form or in the form of larger molecules, for example, natural or synthetic peptides). In particular, there is a continuing need for new labels with different oxidation potentials thereby widening the range of possible assays available and increasing the scope for the development of multiplex reactions.

SUMMARY OF THE INVENTION

The invention provides use as a label in an electrochemical assay of a compound of general formula I:

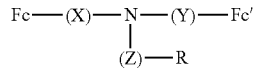

in which:
Fc is a substituted or unsubstituted ferrocenyl moiety,
Fc' is a substituted or unsubstituted ferrocenyl moiety, and may be the same as or different from Fc;
X is a C1 to C6 alkylene chain which is optionally interrupted by —O—, —S—, or —NR$^5$—, in which R$^5$ represents hydrogen or C1 to C6 alkyl;
Y is a C1 to C6 alkylene chain which is optionally interrupted by —O—, —S—, or —NR$^5$—, in which R$^5$ represents hydrogen or C1 to C6 alkyl;
Z is a C1 to C12 alkylene chain which may optionally be substituted and/or may optionally be interrupted by —O—, —S—, cycloalkyl, —CO—, —CONR$^1$—, —NR$^1$CO— or —NR$^1$— in which R$^1$ represents hydrogen or C1 to C4 alkyl; and
R is a linker group.

The compounds used in accordance with the invention have been found to be effective labels for use in electrochemical assays. In particular, the compounds may be used to form labelled substrates. Molecules of interest as substrates that may be labelled include, but are not limited to—amino acids, nucleotides, nucleosides, sugars, peptides, proteins, oligonucleotides, polynucleotides, carbohydrates and derivatives of any of those molecules. Other substrates that might be labelled using the compounds of the invention include latex/paramagnetic microparticles and nanoparticles. The labelling compounds of general formula I and labelled molecules including labels derivable from the labelling compounds are potentially useful in electrochemical techniques in which their electrochemical characteristics can be utilized to derive information about the labels or their environment. For example, the compounds of the invention may find use in a method as described in WO 03/074731 or in a method as described in WO02005/05657.

In the compounds used according to the invention it is preferred that X represents C1 to C6-alkylene optionally interrupted by oxygen; Y represents C1 to C6-alkylene optionally interrupted by oxygen; and Z represents C1 to C8 alkylene optionally interrupted by oxygen. X is is preferably —(CH$_2$)$_x$— in which x is from 1 to 6, preferably 1 to 4, especially 1 or 2; or C1 to C6-alkylene interrupted by oxygen, for example —(CH$_2$)$_3$—O—CH$_2$—, —(CH$_2$)$_2$—O—(CH$_2$)$_2$—, or —CH$_2$—O—(CH$_2$)$_3$—. Y is preferably —(CH$_2$)$_y$— in which y is from 1 to 6, preferably 1 to 4, especially 1 or 2; or C1 to C6-alkylene interrupted by oxygen, for example —(CH$_2$)$_3$, —O—CH$_2$—, —(CH$_2$)$_2$—O—(CH$_2$)$_2$— or —CH$_2$—O—(CH$_2$)$_3$—. Preferably X and Y are the same. Preferably Fc and Fc' are the same and X and Y are the same. Preferably Z is —(CH$_2$)$_z$— in which z is from 1 to 8, with z preferably representing from 1 to 6, especially from 2 to 6; or is C1 to C8 alkylene interrupted by oxygen, for example —((CH$_2$)$_2$—O—(CH$_2$)$_3$— or —(CH$_2$)$_2$—O—(CH$_2$)$_3$—. In one preferred embodiment, X is —(CH$_2$)$_x$— in which x is 1 or 2; Y is —(CH$_2$)$_y$— in which y is 1 or 2; and Z is (CH$_2$)$_z$— in which z is from 1 to 8. Where X and Y represent an alkylene chain interrupted by —NR$^5$—, R$^5$ preferably represents hydrogen or C1 to C4 alkyl, more preferably hydrogen.

In one preferred embodiment, the invention provides use, as an electrochemical label, of a compound of the general formula II:

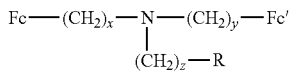

II in which:
Fc is a substituted or unsubstituted ferrocenyl moiety,
Fc' is a substituted or unsubstituted ferrocenyl moiety, and may be the same as or different from Fc;
x is 1 or 2;
y is 1 or 2;
z is from 1 to 8;
and R is a linker group.

Preferably, x and y are each equal to 1.

Ferrocenyl moieties in the compounds of general formula I or general formula II may be unsubstituted ferrocenyl or one or both may be substituted as further disclosed below. It is preferred that the ferrocenyl moieties are the same, and it is therefore preferred that where Fc is substituted with one or more substituents, Fc' carries the same substituents in the same positions.

Except where the contrary is apparent from the context, the term "substrate" is used throughout the remainder of this document to include both naturally occurring substrates and synthetic substrates. Synthetic substrates include synthetic analogues of naturally occurring substrates. Substrates include single nucleotides and single amino acids. In the case of an assay relying upon cleavage of a substrate, for example by an enzyme, a single amino acid may be regarded as a substrate because, although it lacks an internal bond capable of being cleaved by a protease enzyme, such a bond may be formed through the attachment of a marker.

The invention provides a method of detecting a chemical entity using a compound according to the invention. Use in an electrochemical assay according to the invention may be for example in an assay for detecting an electrochemically labelled substrate. The electrochemical assay may for example be an assay for determination of the amount of an electrochemically labelled substrate. The assay may advantageously be for detecting or determining the amount of a labelled substrate wherein the labelled substrate is selected from amino acids, nucleotides, nucleosides, sugars, peptides, proteins, oligonucleotides, polynucleotides, carbohydrates, microparticles and nanoparticles. In certain preferred embodiments, the assay is for detecting or determining the amount of a labelled substrate in which the labelled substrate is selected from nucleotides, nucleosides, oligonucleotides, and polynucleotides. In another advantageous embodiment, the assay is for detecting or determining the amount of a labelled substrate in which the labelled substrate is selected from amino acids, peptides, and proteins.

For the purpose of attachment to substrates, the label may be functionalised by addition of a functionalising group. Thus, the invention further provides functionalised derivatives comprising a moiety derivable from the compounds of the invention attached to a functionalising group suitable for enhancing attachment to a substrate.

The invention also provides a method for manufacturing a functionalized labelling compound comprising a label moiety for use in an electrochemical assay, comprising reacting a compound of general formula I:

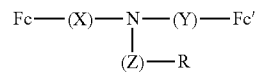

I in which:
Fc is a substituted or unsubstituted ferrocenyl moiety,
Fc' is a substituted or unsubstituted ferrocenyl moiety, and may be the same as or different from Fc;
X is a C1 to C6 alkylene chain which is optionally interrupted by —O—, —S—, or —NR$^5$—, in which R$^5$ represents hydrogen or C1 to C6 alkyl;
Y is a C1 to C6 alkylene chain which is optionally interrupted by —O—, —S—, or —NR$^5$—, in which R$^5$ represents hydrogen or C1 to C6 alkyl;
Z is a C1 to C12 alkylene chain which may optionally be substituted and/or may optionally be interrupted by —O—, —S—, cycloalkyl, —CO—, —CONR$^1$—, —NR$^1$CO— or —NR$^1$— in which R$^1$ represents hydrogen or C1 to C4 alkyl; and
R is a linker group comprising an oxygen atom
with a functionalising compound to obtain a funtionalised labelling compound of general formula III:

A-L-F      III in which A represents

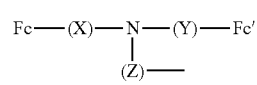

Ia wherein Fc, Fc', X, Y and Z are as defined above with reference to general formula I;
F represents a functionalising moiety, especially a functionalising moiety for reacting with a substrate for attachment of the labelling moiety to the substrate; and
L represents a linker moiety.

The linker moiety L will generally be a linker moiety derivable from the linker group R. For example where R is or contains an OH group L will usually represent or comprise —O—.

Furthermore the invention provides a method for the manufacture of a substrate, comprising reacting a compound of general formula III:

A-L-F      III in which A, F and L are as defined above;
with a substrate to form a labelled substrate.

The invention moreover provides a functionalised labelling compound for use in the manufacture of a substrate, the functionalised labelling compound having the general formula III:

A-L-F      III in which A, L and F are as defined above.

The invention also provides a labelled substrate for use in an electrochemical assay, the labelled substrate being of general formula IIIa:

A-L-F'—[S]      IIIa in which A represents

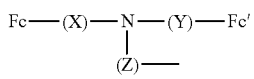

in which:
Fc is a substituted or unsubstituted ferrocenyl moiety,
Fc' is a substituted or unsubstituted ferrocenyl moiety, and may be the same as or different from Fc;
X is a C1 to C6 alkylene chain which is optionally interrupted by —O—, —S—, or —NR$^5$—, in which R$^5$ represents hydrogen or C1 to C6 alkyl;
Y is a C1 to C6 alkylene chain which is optionally interrupted by —O—, —S—, or —NR$^5$—, in which R$^5$ represents hydrogen or C1 to C6 alkyl;
Z is a C1 to C12 alkylene chain which may optionally be substituted and/or may optionally be interrupted by —O—, —S—, cycloalkyl, —CO—, —CONR$^1$—, —NR$^1$CO— or —NR$^1$— in which R$^1$ represents hydrogen or C1 to C4 alkyl;
L-F' represents a linking moiety; and
[S] represents a substrate.
The linking moiety -L-F'— is in general a moiety derivable from the moiety -L-F— according to general formula III.

The invention further provides assays comprising substrates according to the invention.

DETAILED DESCRIPTION

The application of electrochemical detection has a number of advantages over fluorescent detection. Electrochemical detection has the potential for very high levels of sensitivity and exhibits a wider linear dynamic range than fluorescence. There is no requirement for samples to be optically clear. There is also less interference from background contaminants (many biological samples auto-fluoresce).

Electrochemical detection is based on the observation that an electrochemically active marker exhibits different electrochemical characteristics depending on whether or not it is attached to a substrate and on the nature of the substrate. For example, in the case of an electrochemical label attached to an amino acid, the exhibited characteristics will depend not only on the identity of the amino acid but also on whether or not that amino acid residue is incorporated into a peptide or protein, and on the length of any such peptide or protein. Under appropriate circumstances, the electrochemical activity of a marker attached to an amino acid residue can change by a detectable degree following loss of attachment of a single or very few amino acid residues.

The size and characteristics of a molecule to which an electrochemically active marker is attached influence the observable characteristics of the electrochemical marker. That may occur, for example, by influencing the rate of migration of the marker by diffusion or its rate of migration in response to an electric field.

Electrochemical activity of a marker may also be influenced by steric effects resulting from the presence of the molecule to which it is linked. For example, steric hindrance may prevent the marker from approaching an electrode and accepting or donating electrons.

If the marker is attached to a peptide then the secondary structure of the peptide (as largely determined by the primary sequence) may influence the physical properties of the marker. For example, if the marker is attached to an amino acid residue in a peptide such that the structure of the peptide sterically hinders the electrochemically active marker then the signals observable by voltammetry may be reduced. Digestion of the peptide may destroy or release secondary structure elements and thus reduce or abolish the influence of the peptide structure on the marker. Accordingly, digestion of the peptide results in a change, usually an increase, in the electrochemical signal produced by the marker moiety. In a differential pulse voltammetry experiment, the faradaic current response at a particular applied voltage may increase upon digestion of the peptide.

Analogously, if a marker is attached to a nucleotide, the electrochemical characteristics will be influenced by whether or not the nucleotide is incorporated into an oligonucleotide, upon the length of that oligonucleotide, and upon the sequence of the oligonucleotide especially in the vicinity of the point of attachment.

The information relating to the electrochemically active marker can be obtained by voltammetry or by an amperometric method. Differential pulse voltammetry is particularly suitable. If desired, the electrochemical detection step may be carried out using one or more electrodes covered by a membrane which is able selectively to exclude molecules based on one or more characteristics, for example size, charge or hydrophobicity. That may assist in eliminating background noise current arising from, for example, charged species in the solution.

In one embodiment of the invention, the compounds of general formula I used in electrochemical assay are N,N-di-(ferrocenylalkyl)aminoalcohols, the aminoalcohol moiety advantageously having from 2 to 10 carbon atoms, preferably from 2 to 8 carbon atoms, especially from 3 to 6 carbon atoms. Preferably, the alcohol moiety is a straight-chain alcohol moiety that is unsubstituted or substituted and which is optionally interrupted by one or more hetero atoms and/or one or more groups. Illustrative of hetero atoms are, for example, oxygen, sulphur or nitrogen. Groups that may be present include without limitation —O—, —S—, cycloalkyl, including heterocycloalkyl, —CO—, —CONH—, —NHCO— and —NH— and —NR$^1$— in which R$^1$ is C1 to C4 alkyl. Substituents, when present, may be for example C1-C4 alkyl which may optionally be substituted by one of more groups selected from a hydroxy, halo, cyano, oxo, amino, ester or amido; C1-C4 alkenyl; C1-C4 alkenyl substituted with a hydroxy, halo, cyano, oxo, amino, ester or amido; aryl; or aryl substituted with a hydroxy, halo, cyano, oxo, amino, ester or amido.

Preferably, the alkylene moiety of the diferrocenylalkyl group has from 1 to 4 carbon atoms, preferably one or two carbon atoms. Preferably, the alkylene moiety is the same in both ferrocenylalkyl groups. Thus, preferably, the diferrocenylalkyl group is diferrocenylmethyl or diferrocenylethyl, in which the ferrocenyl moiety may in each case independently be unsubstituted or substituted by one or more substituents.

In the compounds (including labelling compounds, functionalised labelling compounds and labelled substrates) used in accordance with the invention, including the compounds according to general formulae I, II and III and the label moiety of general formula Ia, the two ferrocenyl groups Fc and Fc' are each preferably independently selected from unsubstituted and substituted ferrocenyl groups. In one embodiment, the two ferrocenyl groups in the compounds according to general formulae I, II and III and labelling moiety of general formula Ia are each unsubstituted ferrocenyl. In other embodiments, one or both pentadienyl rings of one or each of the ferrocenyl moieties may be substituted by one or more substituents, the nature and location of which are selected so as to influence in a desired manner the redox characteristics of the ferrocene moiety. The pentadienyl rings of the ferrocenyl moiety may additionally or instead be substituted by any ring substituents that do not materially reduce the electrochemical sensitivity of the label. In one embodiment, at least one and preferably both of the ferrocenyl groups are substituted ferrocenyl moieties having one or more substituents selected from halo; C1-C4 alkyl which may optionally be substituted by one of more groups selected from a hydroxy, halo, cyano, oxo, amino, ester or amido; C1-C4 alkenyl; C1-C4 alkenyl substituted with a hydroxy, halo, cyano, oxo, amino, ester or amido; aryl; or aryl substituted with a hydroxy, halo, cyano, oxo, amino, ester or amido. Preferred substituents include C1 to C4 alkyl, for example methyl or ethyl; C1-C4 alkyl substituted with $NH_2$, $NHR^2$, $NR^3R^4$ in which R2, R3 and R4 are each independently selected from straightchain or branched C1 to C4 alkyl; halo for example bromo or fluoro; or C1 to C4 alkenyl, for example vinyl.

For example, in one embodiment of the invention, each ferrocenyl group includes a single substituent at a ring position adjacent to the position at which the ferrocenyl group is attached to the rest of the molecule. Illustrative of that embodiment is the compound bis((2-(dimethylamino)ferrocenyl)methyl)-6-aminohexanol. In another embodiment both ferrocenyl groups are unsubsituted. Illustrative of that embodiment is the compound N,N-di(ferrocenylmethyl)-6-aminohexanol. Further illustrative ferrocenyl groups include 1'-methyl ferrocenyl; 2-methylferrocenyl; 1'-vinylferrocenyl; 1'-bromoferrocenyl; and 2,3,4,5-tetramethyl-1',2',3',4',5'-pentamethylferrocenyl.

It is preferred that the ferrocenyl moieties are identical. That is thought to give a stronger signal.

The moiety Z may be unsubstituted or substituted. Substituents, when present, may be for example one or more substituents selected from hydroxy, halo, cyano, amino, and unsubstituted or substituted C1-C4 alkyl, C1-C4 alkenyl, or aryl; wherein in each case optional substituents include without limitation hydroxy, halo, cyano, oxo, amino, ester or amido. The moiety Z may, if desired, be interrupted by one, or optionally more than one, atom or moiety seleted from —O—, —S—, cycloalkyl, including heterocycloalkyl, —CO—, —CONH—, —NHCO— and —NH— and —$NR^1$— in which $R^1$ is C1 to C4 alkyl. Illustrative of cycloalkyl moieties that may be included as interruptions within the moiety Z are cycloalkyl rings with from 5 to 7 ring atoms, especially 6 ring atoms, for example cyclohexyl, piperidinyl, morpholinyl.

The moieties X and Y, which are preferably the same, advantageously have a chain length of from 1 to 6, preferably from 1 to 4 carbon atoms, especially one or two carbon atoms, and more especially one carbon atom. The moieties X and Y may each represent an alkylene chain, optionally interrupted by —O—, —S— or —$NR^5$— for example —NH—. Preferred moieties X and Y include, for example, —$CH_2$—, —$CH_2$—$CH_2$—, —$(CH_2)_3$—O—$CH_2$—, —$CH_2$—O—$(CH_2)_3$—, —$(CH_2)_3$—O—$(CH_2)_2$—, and —$(CH_2)_2$—O—$(CH_2)_3$—.

Linkage to the substrate can be by any suitable linkage, typically by linkage to a substrate side chain. The linker group R in the compounds of general formula I may be any group suitable for effecting linkage to the substrate either directly or via a functionalising group as described herein. R is preferably a hydroxyl group or a protected hydroxyl group or a group containing a hydroxyl group or a protected hydroxyl group. It will be appreciated, however, that any other suitable linker group R may be selected having regard to the substrate to which, in use, the compound is to be attached. Various synthetic methods have been developed for the derivatisation of protein, peptide or amino acid side chains or protein, peptide or amino acid terminal moieties. For example, lysine residues in a protein may be derivatised by reaction with a succinimidyl ester. For derivatisation at other amino acid residues, other known synthetic methods may be used. For example, a maleimide reagent may be used to derivatise cysteine residues. An N-hydroxy succinimide ester may be used to derivatise the amino terminus or side chain amino group of a protein or peptide, or an amino moiety of an amino acid.

Suitable derivatisation methods for nucleotides are also well-known, for example, using the phosphoramidite moiety.

The above derivatisation methods are illustrative of the methods that may be used to link the compounds of the invention to a substrate, although other methods may be used.

Labelled substrates according to the invention may be prepared by reaction of a compound according to the invention, optionally after functionalisation to obtained a functionalised labelling compound, with a substrate, for example, with a substrate selected from amino acids, nucleotides (for example oligo deoxyribonucleotides or oligo ribonucleotides), nucleosides, sugars, peptides, proteins, oligonucleotides, polynucleotides, carbohydrates and derivatives of any of those molecules.

In a preferred embodiment, the substrate is a nucleotide or an oligonucleotide. The nucleotide may be selected from adenosine, thymidine, guanosine, cytidine or uridine. Preferably the nucleotide, or a nucleotide of the oligonucleotide, is attached to the label through a group attached to the ribose or deoxyribose group of the nucleotide, for example in the 2', 3' or 5' position, for example through an oxygen or nitrogen atom. Most preferably, the nucleotide is attached at the 3' or 5' position, for example at the 5' position. Linking at other positions is also possible.

In the case of nucleotides, one advantageous way of attaching labels of the invention is by functionalisation with phosphoramidite. The linking of phosphoramidite groups to oligonucleotides is widely practised in oligonucleotide synthesis and thus methods and conditions for attachment to an oligonucleotide of labels functionalised with phosphoramidite will be well-known and a routine matter to those skilled in the art. Further, it advantageously permits the use of standard oligo manufacturing methods.

Oligonucleotides to be for use in an assay in accordance with the invention are advantageously nucleotides having from 2 to 50 nucleotides, more preferably from 2 to 40 nucleotides especially from 15 to 35 nucleotides, with from 18 to 30 nucleotides being especially preferred. For some applications, shorter oligonucleotides may be useful, for example oligonucleotides with from 2 to 14 nucleotides, more preferably from 2 to 10 nucleotides.

Attachment to proteins, for example via cysteine, lysine, may be accomplished in some cases by incubation of the protein and ferrocenyl label together at room temperature in an appropriate buffer solution. Where the label is advantageously to be linked to cysteine or lysine but the substrate sequence does not contain cysteine or lysine at a suitable position the sequence may if desired be mutated to add one or more cysteine or lysine residue either as an additional residue or as a substitution for another residue. An alternative method for attachment to proteins may include biotinylation of the labels and use of commercial streptavidinated proteins (or vice versa). By way of example, the substrate may be biotinylated by any standard technique for example by use of a commercially available biotinylation kit. Biotinylated substrate will bind to strepavidin or avidin conjugated compounds such as antibodies (which are commercially and widely available).

It will however be apparent to the skilled person that similar labels may be attached to a substrate at a selected one of a number of locations by use of an appropriate labelling functional group.

In functionalised labelling compounds of the general formula III:

A-L-F    III

A-L is preferably a moiety derived from a compound according to general formula I and F is a functionalising group. Preferred functionalised labelling compounds of the general formula III include compounds of the general formula IIIb:

A-O—F    IIIb wherein A-O is a moiety derived from a compound according to general formula I, preferably by loss of a hydroxy hydrogen atom or protecting group when the linker group R of general formula I is hydroxyl or a hydroxyl-containing group or is a protected hydroxyl group, and F is a functionalising group.

Suitable functionalising groups that may be usable with labels of the invention, including as functionalising group F in general formula III and general formula IIIb, may include, without limitation, succinimidyl ester groups, phosphoramidite groups, maleimide groups, biotin and azide groups. It will be appreciated, however, that there may be used any functionalising group that facilitates attachment of the labelling compound to the substrate to be labelled.

The invention also provides a method of detecting a nucleic acid (for example RNA or DNA) in a sample comprising the optional step of amplifying the nucleic acid (for example by PCR or another nucleic acid amplification technique) followed by the step of contacting the amplicon with a complementary nucleic acid probe under conditions to allow hybridization between the probe and amplicon, followed by the step of selectively degrading either hybridized or unhybridized probe (for example by use of single or double strand specific nucleases), wherein said probe is labelled with an electrochemically active compound of the invention and wherein the method provides the step of measuring the electrochemical activity of the compound labelling the probe of wherein said electrochemical activity is dependent either quantitatively or qualitatively on the extent of degradation of the probe.

The invention also provides a method of detecting an antibody or derivative (which may for example be bound to target antigen in an assay) with an electrochemically active compound of the invention comprising the step of measuring the electrochemical activity of the compound.

The invention also provides methods of diagnosing or monitoring a disease in a subject comprising using a method of the invention in the detection of a protease or a protease inhibitor associated with said disease in a tissue or body fluid of the subject.

The invention also provides methods of diagnosing or maintaining a disease in a subject comprising using a method of the invention to detect a peptide or protein associated with said disease in a tissue or body fluid of the subject.

The invention also provides methods of diagnosing or monitoring a disease in a subject comprising using a method of the invention in the detection of a nuclease or a nuclease inhibitor associated with said disease in a tissue or body fluid of the subject.

Furthermore, the invention provides use of a method of the invention for detecting a disease in a subject.

The invention also provides methods of detecting a pathogen or other undesirable organism, for example a food spoilage organism, comprising using a method of the invention.

Moreover, the invention provides the use of a N,N-di(ferrocenylalkyl)glycine derivative, for example a N,N-di(ferrocenylalkyl)glycinamido derivative, as an electrochemical label in an electrochemical measurement method.

The invention also provides an assay comprising a labelled substrate of the invention, optionally in combination with other assay components for example a sample vessel, a container comprising electrodes for electrochemical detection, enzymes for use in the assay or standards and controls. Said assay may comprise more than one different labelled substrate of the invention. If that is the case the presence of different labelled substrates may be differentially detected by labelling them with electrochemical labels of the invention having different electrochemical characteristics (for example different oxidation potentials) thereby permitting the assay to be a multiplex (for example a duplex) assay in which different substrates may be discriminated when present in the same sample vessel.

The invention provides in an additional embodiment a compound according to general formula I

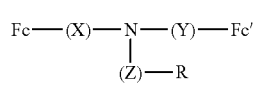

I in which:

Fc is a substituted ferrocenyl moiety,

Fc' is a substituted ferrocenyl moiety, and may be the same as or different from Fc;

X is a C1 to C6 alkylene chain which is optionally interrupted by —O—, —S—, or —NR$^5$—, in which R$^5$ represents hydrogen or C1 to C6 alkyl;

Y is a C1 to C6 alkylene chain which is optionally interrupted by —O—, —S—, or —NR$^5$—, in which R$^5$ represents hydrogen or C1 to C6 alkyl;

Z is a C1 to C12 alkylene chain which may optionally be substituted and/or may optionally be interrupted by —O—, —S—, cycloalkyl, —CO—, —CONR$^1$—, —NR$^1$CO— or —NR$^1$— in which R$^1$ represents hydrogen or C1 to C4 alkyl; and R is a linker group.

In that embodiment it is preferred that each ferrocenyl moiety is substituted by at least one substituent selected from halo, C1 to C4-alkyl, haloalkyl, aryl, C1 to C4 alkenyl, and cyano.

In a further additional embodiment, the invention provides a compound according to general formula I

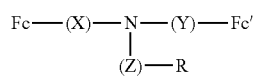

I in which:

Fc and Fc' are each an unsubstituted ferrocenyl moiety,

X is a C1 to C6 alkylene chain which is optionally interrupted by —O—, —S—, or —NR$^5$—, in which R$^5$ represents hydrogen or C1 to C6 alkyl;

Y is a C1 to C6 alkylene chain which is optionally interrupted by —O—, —S—, or —NR$^5$—, in which R$^5$ represents hydrogen or C1 to C6 alkyl;

Z is a C6 to C12 alkylene chain or is a C1 to C12 alkylene which is substituted by one or more substituents and/or is interrupted by a moiety selected from —O—, —S—, cycloalkyl, —CO—, —CONH—, —NHCO— or —NR$^1$— in which R$^1$ represents hydrogen or C1 to C4 alkyl; and R is a linker group.

In that further additional embodiment, it is preferred that X represents —(CH$_2$)$_x$— in which x is from 1 to 6; and Y represents —(CH$_2$)$_y$— in which y is from 1 to 6.

In the said additional and further additional embodiments, Z preferably represents C6 to C8 alkylene optionally interrupted by oxygen. Preferably, the linker group R comprises a group capable of reacting with a compatible group of a functionalising moiety or of a substrate to attach the compound to said functionalising moiety or said substrate, for example R may be hydroxy, protected hydroxy or a moiety containing a hydroxy or protected hydroxy group.

Table 1 below sets out in the general formulae IVa, Va, VIa, VIIa and VIIIa certain preferred compounds according to the invention which may be used as labels in electrochemical assays in accordance with the invention, and which may be used to make functionalised labelling compounds and labelled substrates according to the invention. Table 1 also sets out in the general formulae IVb, Vb, VIb, VIIb and VIIIb illustrative corresponding functionalised labelling compounds according to the invention. In the formulae in Table 1, except where considerations of steric hindrance mitigate against it, each ferrocenyl may have more than one substituent R, which may be the same or different, and in any ring position. Where there is one or more substituent on one of the ferrocenyl groups, the other ferrocenyl group is to be understood as having the same substituent(s) in the same positions.

TABLE 1

Illustrative compounds and functionalised labelling compounds

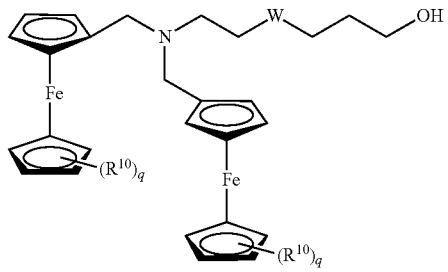

IVa in which R$^{10}$ if present represents halo, C1 to C4-alkyl, haloalkyl, especially fluoroalkyl, phenyl, C1 to C4 alkenyl, for example vinyl, or cyano; q represents from 0 to 5, for example 1; and W represents (CH$_2$)$_n$ where n is from 0 to 6, O, S or NR$^{20}$ where R$^{20}$ is alkyl, for example C1 to C4 alkyl

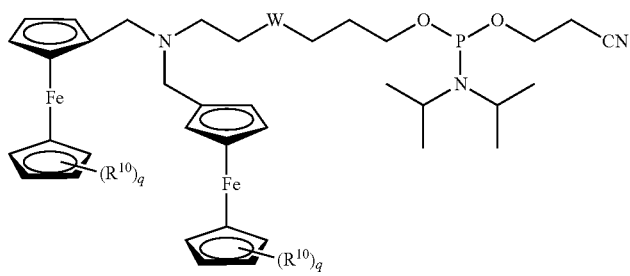

IVb

In which R$^{10}$, q and W are as defined with reference to general formula IVa

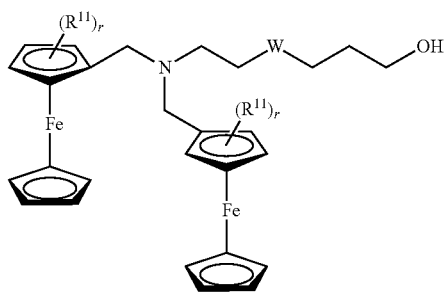

Va

TABLE 1-continued

Illustrative compounds and functionalised labelling compounds in which $R^{11}$ if present represents alkyl, for example C1 to C4-alkyl, aryl, for example phenyl, or amino alkyl, especially dialkyl-substituted amino alkyl, for example di(C1-C4-alkyl)aminomethyl-; r represents from 1 to 4, for example 1; and W represents $(CH_2)_n$ where n is from 0 to 6, O, S or $NR^{20}$ where $R^{20}$ is alkyl, for example C1 to C4 alkyl

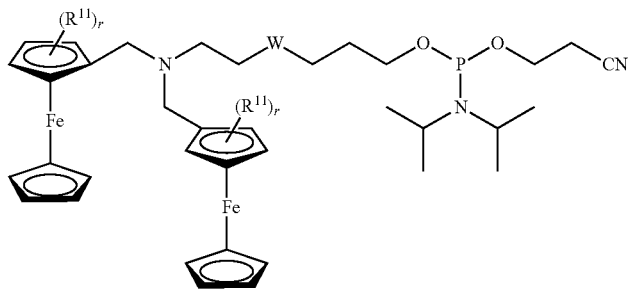

Vb

In which $R^{11}$, r and W are as defined with reference to general formula Va

VIa

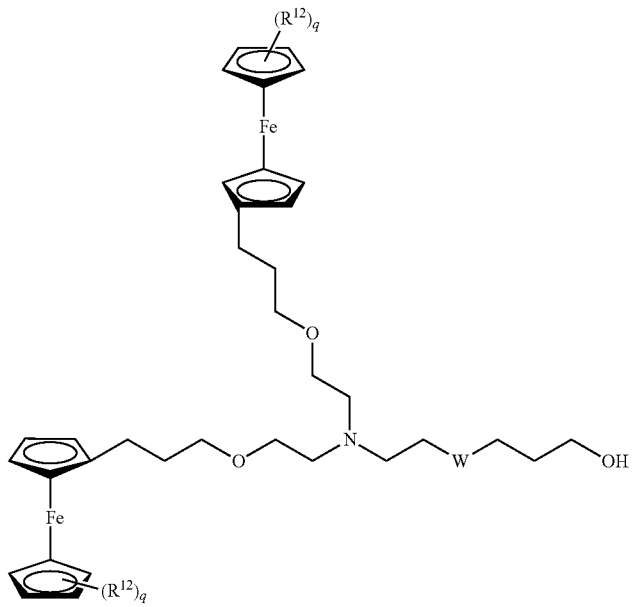

in which $R^{12}$ if present represents halo, C1 to C4-alkyl, haloalkyl, especially fluoroalkyl, phenyl, C1 to C4 alkenyl, for example vinyl, or cyano; q represents from 0 to 5, for example 1; and W represents $(CH_2)_n$ where n is from 0 to 6, O, S or $NR^{20}$ where $R^{20}$ is alkyl, for example C1 to C4 alkyl TABLE 1-continued Illustrative compounds and functionalised labelling compounds

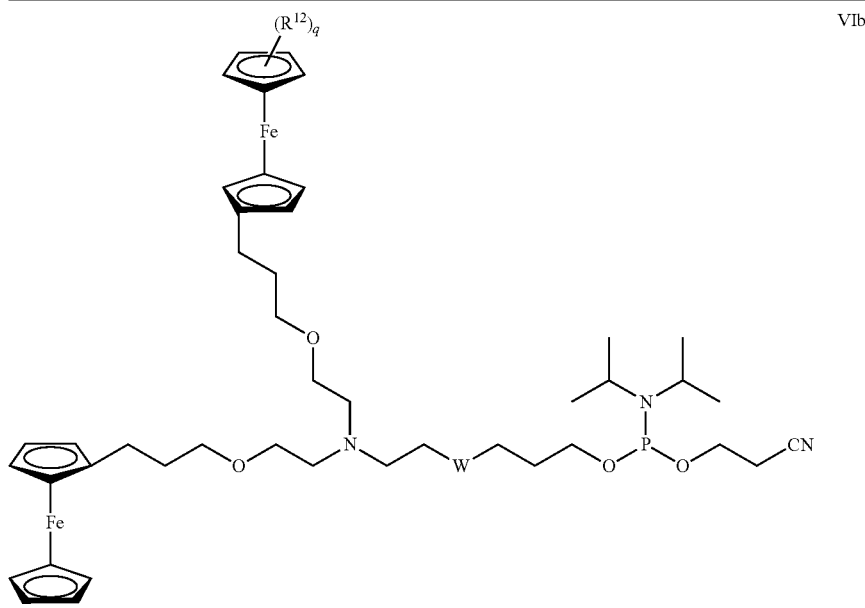

VIb

In which $R^{12}$, q and W are as defined with reference to general formula VIa

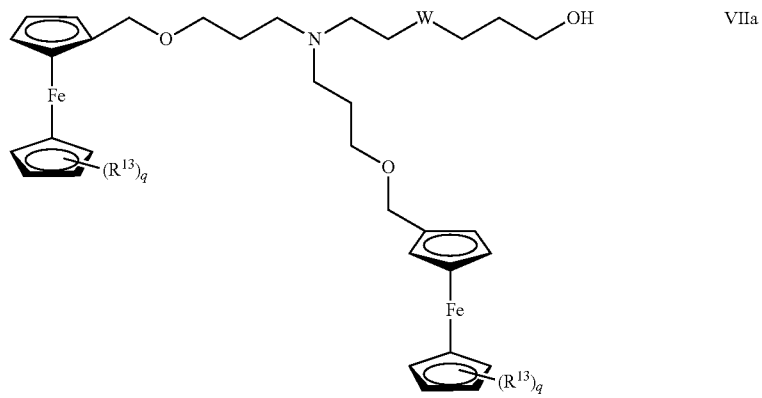

VIIa in which $R^{13}$ if present represents halo, C1 to C4-alkyl, haloalkyl, especially fluoroalkyl, phenyl, C1 to C4 alkenyl, for example vinyl, or cyano; r represents from 1 to 4, for example 1; and W represents $(CH_2)_n$ where n is from 0 to 6, O, S or $NR^{20}$ where $R^{20}$ is alkyl, for example C1 to C4 alkyl

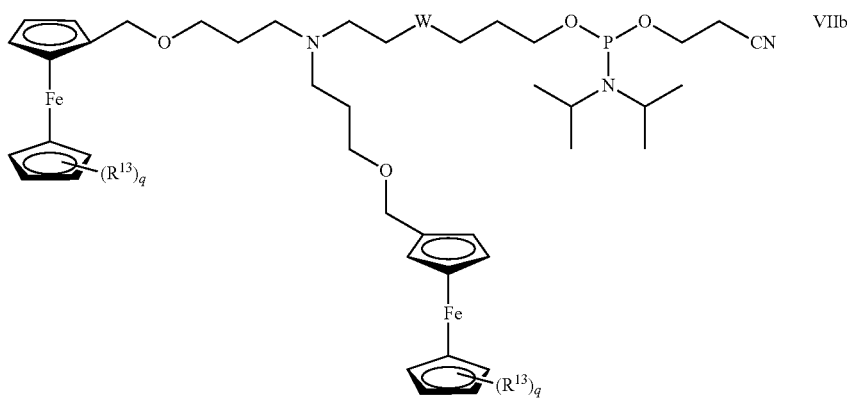

VIIb

TABLE 1-continued

Illustrative compounds and functionalised labelling compounds

In which $R^{13}$, r and W are as defined with reference to general formula VIIa

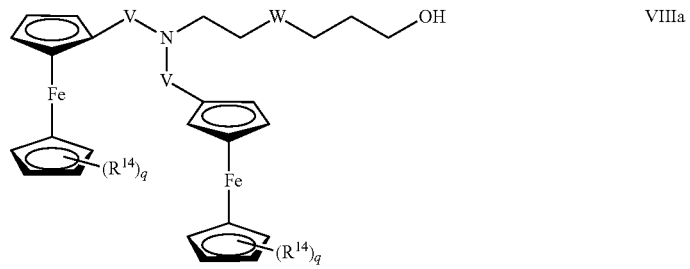

VIIIa in which $R^{14}$ if present represents halo, C1 to C4-alkyl, haloalkyl, especially fluoroalkyl, phenyl, C1 to C4 alkenyl, for example vinyl, or cyano; q represents from 0 to 5, for example 1; W represents $(CH_2)_n$ where n is from 0 to 6, O, S or $NR^{20}$ where $R^{20}$ is alkyl, for example C1 to C4 alkyl; and V represents $(CH_2)_m$ where m represents from 2 to 6

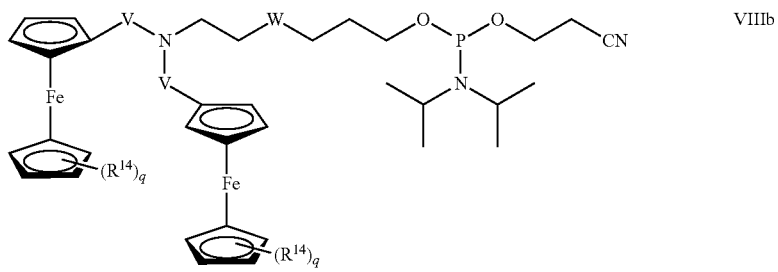

VIIIb

In which $R^{14}$, q, W and V are as defined with reference to general formula VIIIa In the general formulae IVa, Va, VIa, VIIa and VIIIa and their functionalised counterparts in Table 1, when one or more ring substituents $R^{11}$ or $R^{13}$, is present on the proximal pentadienyl ring of each ferrocenyl, that is, the ring that is directly bonded to the rest of the molecule, there is preferably a said ring substituent at an adjacent ring position to that bond. When more than one ring substituent $R^{11}$, $R^{13}$ is present on each proximal pentadienyl ring, those substituents may be in any position relative to one another. When more than one ring substituent $R^{10}$, $R^{12}$ or $R^{14}$ is present on each distal pentadienyl ring of each ferrocenyl, that is the ring remote from the bond linking the ferrocenyl to the rest of the molecule, those substituents may be in any position relative to one another. Whilst in general formulae IVa, Va, VIa, VIIa and VIIIa and their functionalised counterparts in Table 1 there are shown ring substituents on either the proximal or the distal ring, it is also possible for both pentadienyl rings of each ferrocenyl to carry one or more substituents.

In an especially preferred embodiment the compound is N,N-di(ferrocenylmethyl)-6-aminohexanol (referred to in the Examples below as Label A). Other preferred labels that may be used in accordance with the invention include:
2-((diferrocenylmethyl)amino)-1-(4-(hydroxymethyl)piperidin-1-yl)ethanone; and
N,N-di-(ferrocenylmethyl)-2-aminoethoxy) ethanol
in which the or each ferrocenyl moiety may be unsubstituted or substituted by one or more substituents. The compound N,N-diferrocenylmethyl-6-aminohexanol, in which the ferrocenyl groups are both unsubstituted, has been found to have good electrochemical characteristics. As illustrated in the Examples herein, incorporation of one or more substituents on each of the ferrocenyl groups (the substituents in each ferrocenyl being the same) in that compound can be used to obtain compounds with modified electrochemical characteristics, providing through appropriate substituent selection a suite of compounds from which two or more may be selected for the purpose of multiplex reactions.

Certain illustrative compounds according to the invention which have been found to have good electrochemical properties are set out in Table 2:

TABLE 2

Illustrative labelling compounds according to the invention

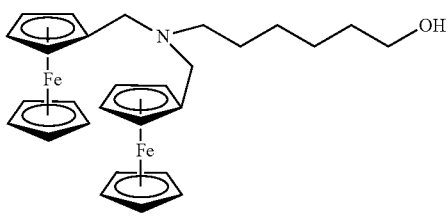

TABLE 2-continued
Illustrative labelling compounds according to the invention
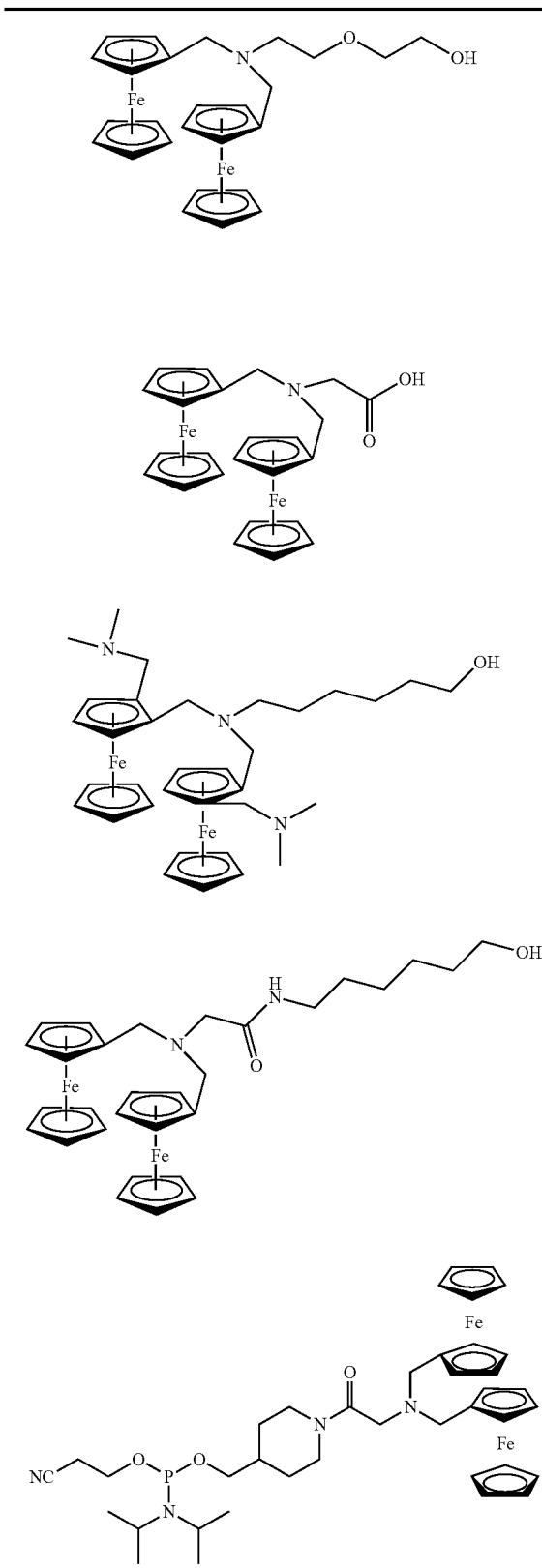
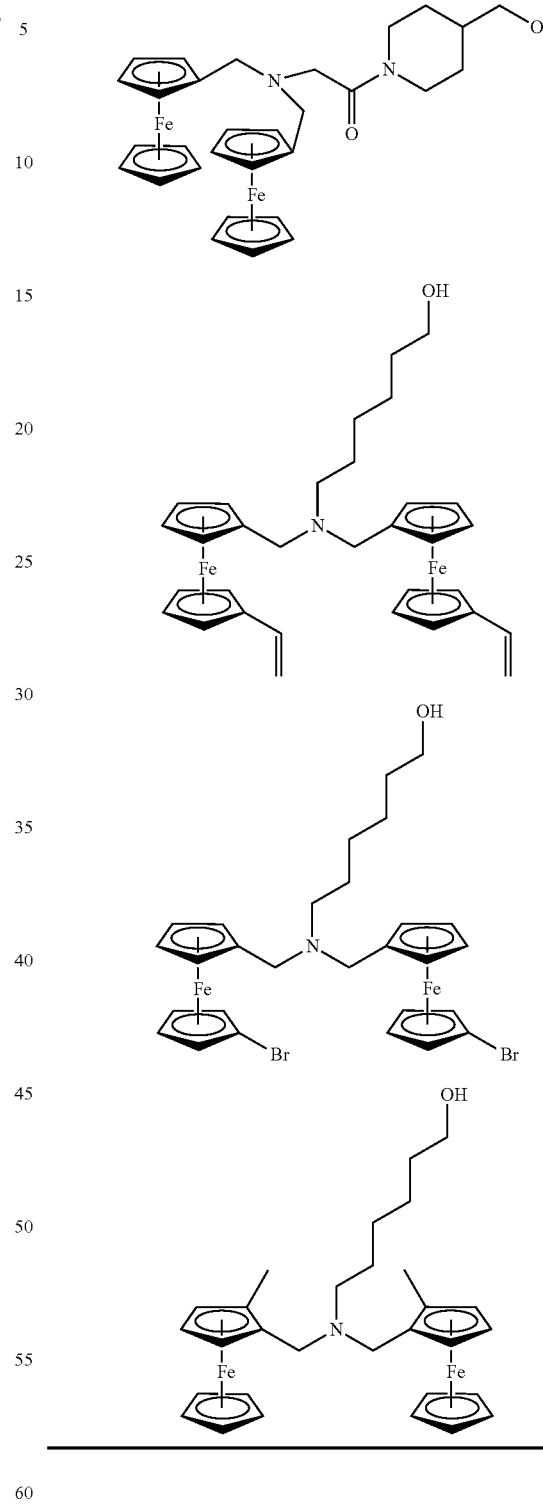
BRIEF DESCRIPTION OF THE DRAWINGS
FIG. 1 is a schematic representation of an electrochemical cell used in differential pulse voltammetry measurements described herein;
FIG. 2 is a differential pulse voltammogram of Label A as manufactured in Example 1 below;

Figure 12A:
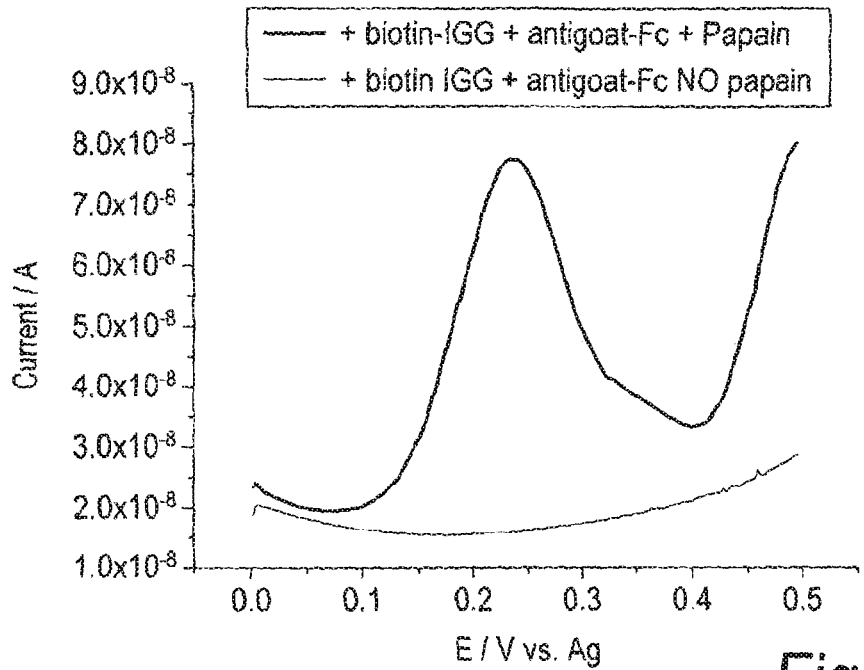
Figure 12B:
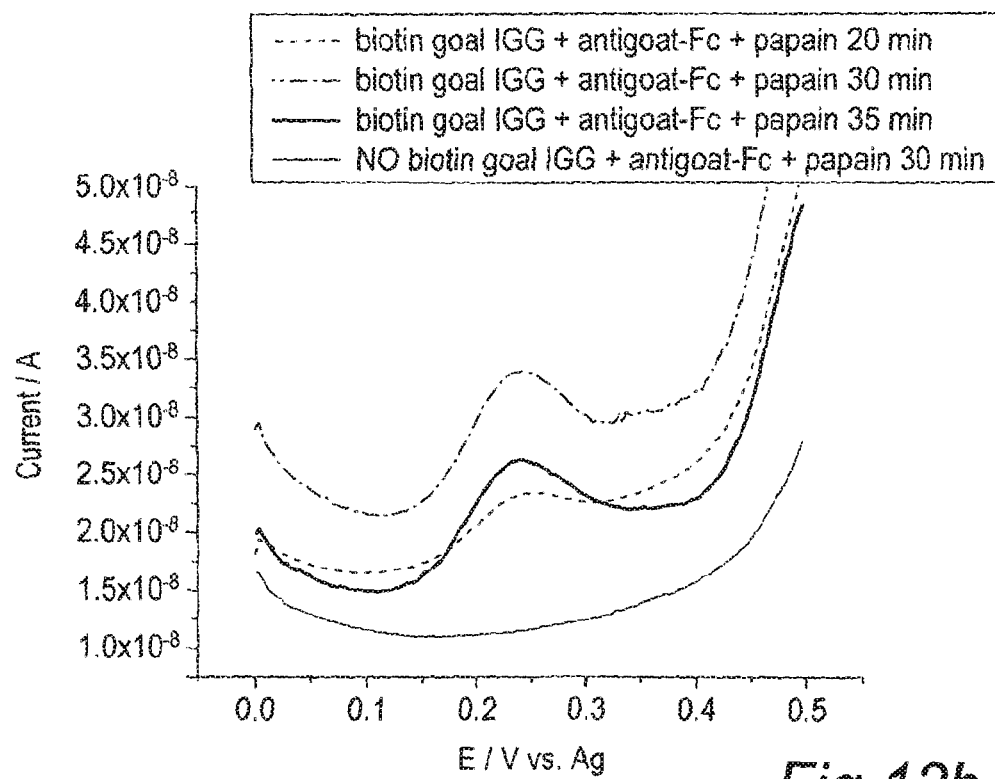
Figure 13:
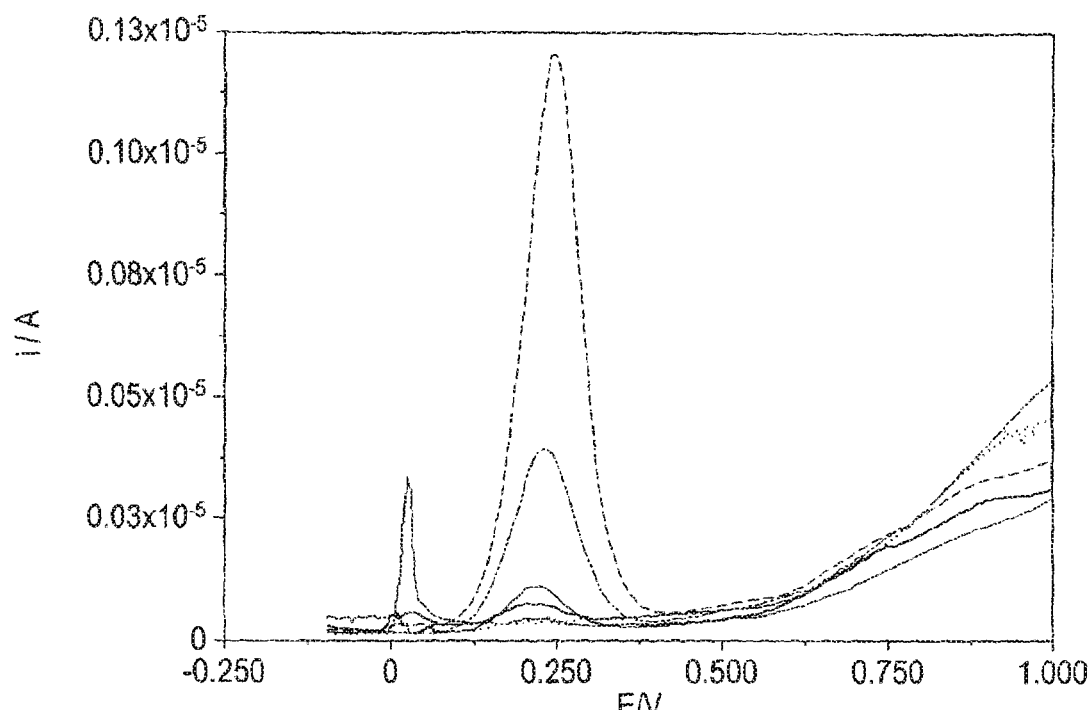
Figure 14:
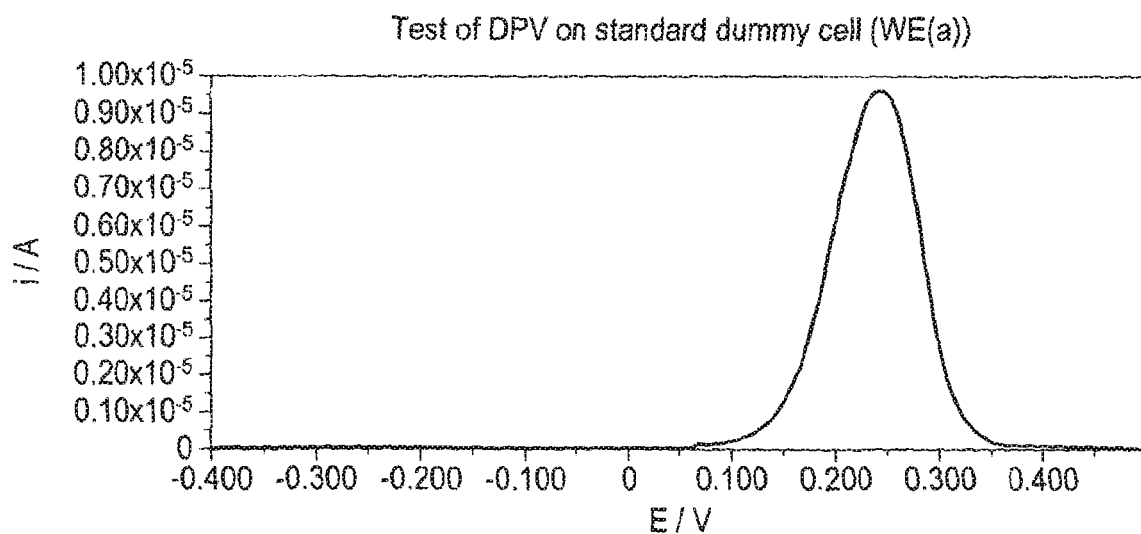

FIG. 12*a* is a voltammetric scan using label A coupled to a commercially available anti-goat IgG;

FIG. 12*b* shows voltammetric scans carried out at time intervals using label A coupled to a commercially available anti-goat IgG;

FIG. 13 shows voltammetric scans of microparticles according to Example 8 at various concentrations; and FIG. 14 is a differential pulse voltammogram of Label D as manufactured in Example 9 below.

DETAILED DESCRIPTION OF CERTAIN PREFERRED EMBODIMENTS

Figure 1:
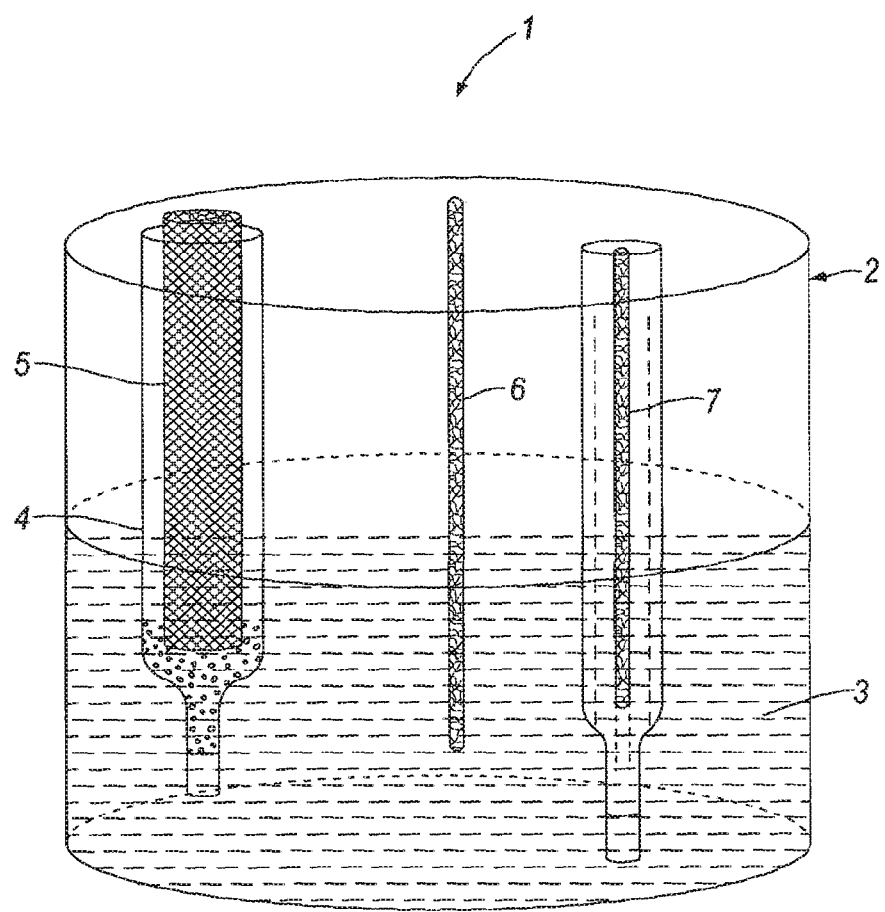

With reference to FIG. 1, there is shown schematically an electrochemical cell 1 suitable for use in the cyclic voltammetry experiments described herein. The cell comprises a vessel 2, containing a background electrolyte solution 3, which is an aqueous 100 mM solution of sodium chloride. Immersed in the solution 3 is a printed carbon working electrode 5, a printed carbon counter electrode 6 and a silver/silver chloride reference electrode 7, all with silver connectors. The sample is spread on to the surface of the working electrode and voltammetry is performed by connecting the silver connectors to the appropriate leads on the potentiometer. By way of illustration, the sample may be prepared as follows: Ferrocenyl label precursor (2 ng) is dissolved in DMSO (1 mL). An aliquot of 10 μL is taken of this solution and is then further diluted in the buffer (500 μL). Then an aliquot (20 μL) is applied to the screen printed electrode to run the electrochemical scan.

The following Examples illustrate the invention:
Materials and Methods—Label Synthesis and Assays
Ferrocene carboxylic acid was obtained from Sigma-Aldrich. Ferrocene carboxaldehyde was obtained from Sigma-Aldrich.
6-Aminohexanol was obtained from Sigma-Aldrich.
Glycine was obtained from Sigma-Aldrich
N,N-diisopropylethylamine was obtained from Sigma-Aldrich.
2-cyanoethyldiisopropylchlorophosphoramidite was obtained from Sigma-Aldrich. Papain solution at concentration 1 mg/mL was obtained from Sigma-Aldrich.
Anti-goat IgG and Biotinylated goat IgG were obtained from Sigma.
PCR methods were performed using a PTC-100 or PTC-200 Programmable Thermal Controller (MJ Research Inc.), or a PeqLab flat bed thermocycler
Streptavidin coated microtitre wells were Sigma Screen™ high density wells.
Materials and Methods—Electrochemical Detection The electrodes are ink based and are screen printed on to a polymer substrate (for example Mylar) followed by heat curing—produced by GM Name plate (Seattle, Wash.)

Example 1—Synthesis of N,N-diferrocenylmethyl-6-aminohexanol [Label A]

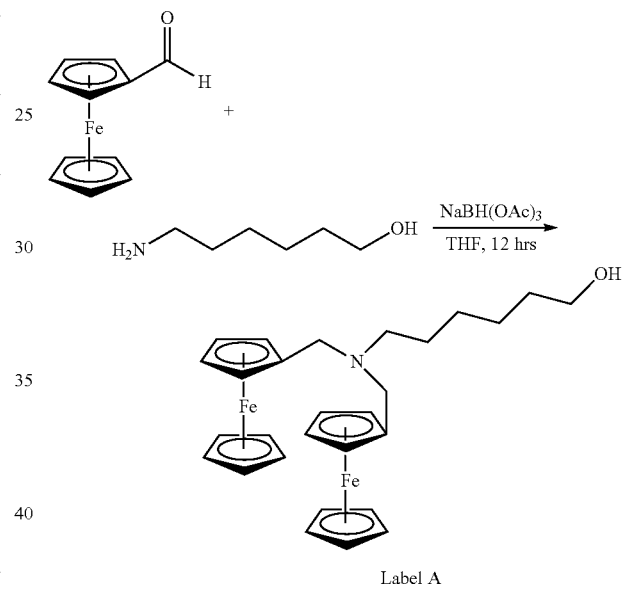

Label A

Ferrocene carboxaldehyde (2.1 g, 9.81 mmol) and 6-aminohexan-1-ol (0.5 g, 4.27 mmol) in dry THF (25 mL) were added to an oven dried flask. Sodium triacetoxyborohydride (2.3 g, 10.90 mmol) was added portionwise to the solution. The reaction was left overnight. The reaction was taken up in ethyl acetate (40 mL), the organic layer was washed with $NaCO_3$ (sat; 20 mL), Brine (20 mL) and MilliQ water (20 mL). The organic fraction was then dried over Magnesium sulfate and the solvent removed in vacuo. The crude product is then columned using 9:1 solution B:solution A (solution A: ethyl acetate 95% TEA 5%, solution B: Petroleum ether 40-60 95%, TEA 5%) to elicit the pure product (dark orange solid). 85% Yield $^1$H NMR (300 MHz, $CDCl_3$) δ 4.18 (2H, s, Cp), 4.17 (2H, s, Cp), 4.13 (15H, s, Cp), 3.66 (4H, t, J=6.25 Hz, $CH_2$), 3.48 (2H, s, $CH_2$), 2.20 (2H, t, J=6, $CH_2$), 1.59-1.31 (6H, m, $CH_2$). $^{13}$C NMR (75.5 Hz, $CDCl_3$) δ 77.83, 77.40, 76.98, 70.58, 68.88, 63.36, 53.02, 52.17, 33.10, 27.43, 25.88. HRMS (ESI) calculated for $C_{28}H_{33}N_1O_1Fe_2$ m/z 519.1430 found 519.1438.

Figure 2:
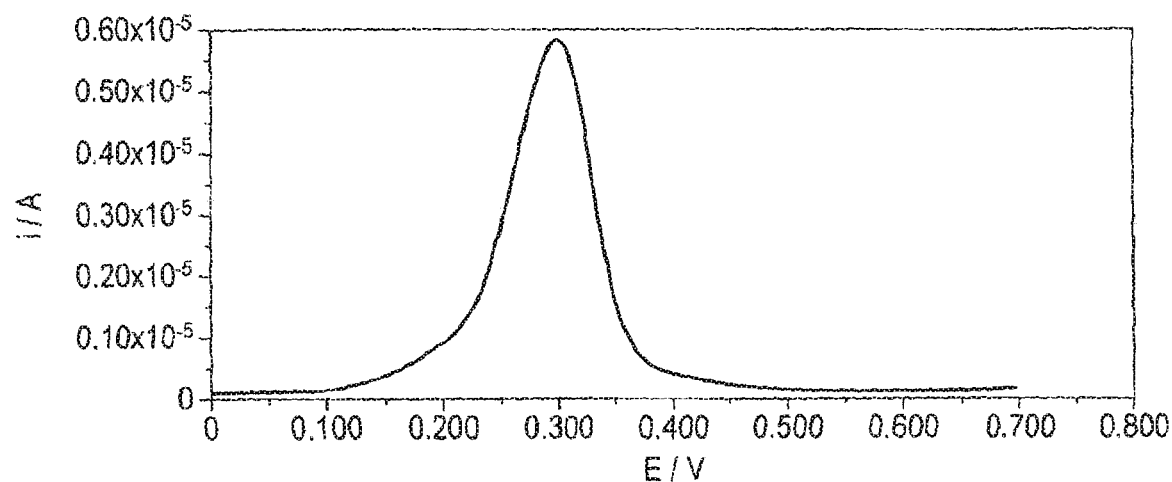

The electrochemistry of compound Label A is shown on the voltammogram of FIG. 2.

The product label was found to have a redox potential of 0.275V.

Example 2—Synthesis of di-((dimethylamino)methylferrocenylmethyl)-6-aminohexanol (Label B)

(a) Synthesis of Dimethylamino)methyl ferrocenecarboxaldehyde (Diaminomethyl)methylferrocene (1 g, 5 mmol) was dissolved in $Et_2O$, n-butyl lithium (2.51 mL, 6.25 mmol) was added slowly and the reaction mixture was stirred at room temperature for 16 hrs.

After 16 hrs, the reaction mixture was quenched with DMF (0.4 mL, 6.25 mmol) and stirred again at room temperature for 4 hrs. Water (15 mL) was then added to the reaction. The organic phase was then extracted with ether (2×25 mL). The combined organic phases were dried with magnesium sulphate, filtered and the solvent was removed under vacuum to afford the product in an 72% yield (dark red/brown oil). $^1$H NMR (300 MHz, $CDCl_3$) δ 9.81 (1H, s, CHO), 4.21 (2H, s, Cp), 4.14 (5H, s, Cp), 3.64 (2H, s, $CH_2$), 2.08 (6H, s, $NMe_2$) $^{13}$C NMR (75.5 Hz, $CDCl_3$) δ 193.2, 86.7, 83.4, 77.8, 77.5, 77.0, 76.62, 75.8, 71.8, 70.3, 70.2, 70.0, 68.4, 68.0, 59.2, 56.6, 44.8, 44.7. HRMS (ESI) calculated for $C_{14}H_{18}N_1O_1Fe_1$ m/z 272.0737 found 272.0731 Ref: Biot, C., Glorian, G., Maciejewski, L. A., Brocard, J. S., Domarle, O., Blampain, G., Millet, P., Georges, A. J., Abessolo, H., Dive, D., Lebibi, *J. J. Med. Chem.* 1997, 40, 3715-3718.

(b) Synthesis of Label B

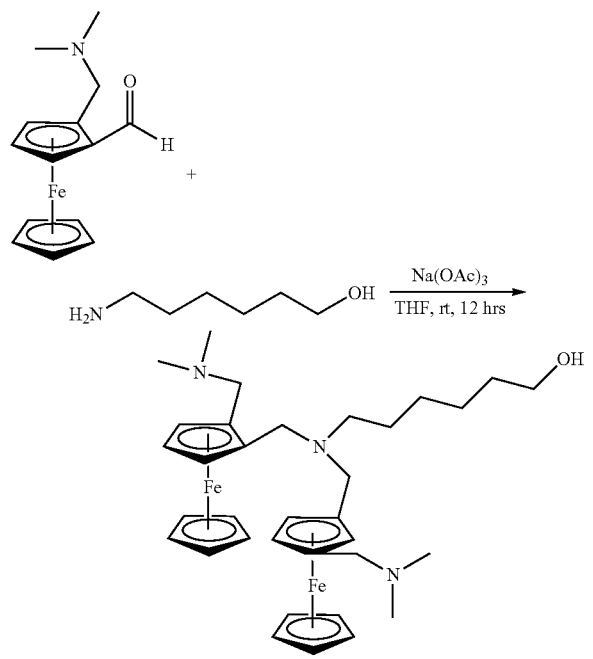

Label B (Dimethylamino)methyl ferrocenecarboxaldehyde (1.1 g, 4.04 mmol) was dissolved in dry THF (30 mL). 6-aminohexan-1-ol (0.25 g, 2.13 mmol) was added. Then sodium triacetoxyborohydride (1.3 g, 6.16 mmol) was added to the reaction mixture. The solution was stirred under nitrogen at room temperature overnight. Ethyl acetate (20 mL) and 1N NaOH (sat; 20 mL) were then added and the organic layer was then extracted with $NaCO_3$ (25 mL), Brine (25 mL) and Milli Q filtered water (25 mL) then dried over $MgSO_4$ and the solvent removed in vacuo to yield an orange oil (0.95, 75%). 1H NMR (300 MHz, $CDCl_3$) δ 4.18 (2H, s, Cp), 4.17 (2H, s, Cp), 4.13 (15H, s, Cp), 3.66 (4H, t, J=6.25 Hz, $CH_2$), 3.48 (2H, s, $CH_2$), 2.20 (2H, t, J=6, $CH_2$), 2.17 (12H, s, $CH_3$) 1.59-1.31 (6H, m, $CH_2$). HRMS (ESI) calcd for $C_{34}H_{49}N_3O_1Fe_2$ m/z 627.3012 found 627.3126.

Figure 3:
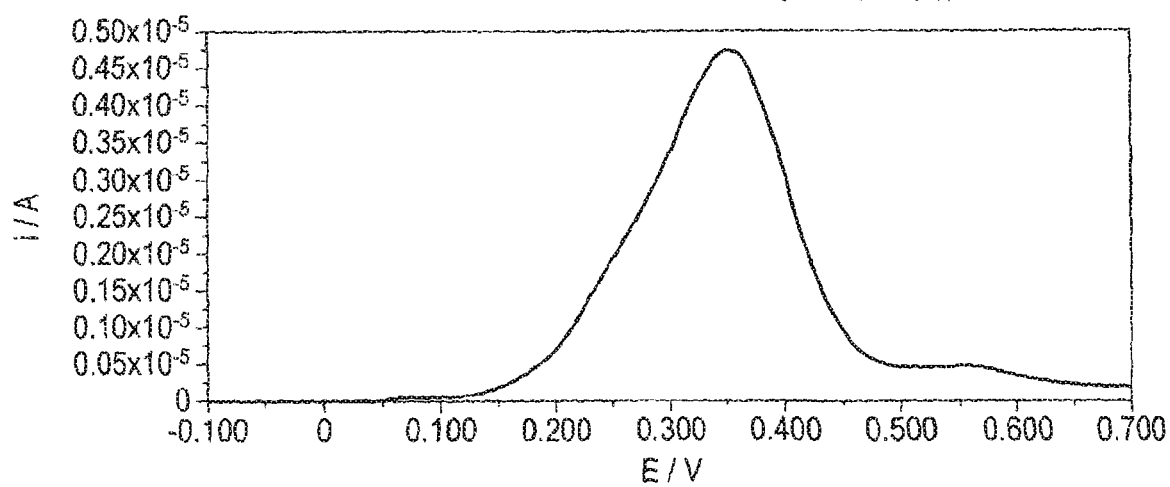
FIG. 3 is a differential pulse voltammogram of Label B as manufactured in Example 2 below.

The electrochemistry of the product compound is shown on the voltammogram in FIG. 3. The product label B was found to have a redox potential of 0.38V.

Example 3: Synthesis of 2-((diferrocenylmethyl)amino)-1-(4-(hydroxymethyl)piperidin-1-yl)ethanone (Label C)

(a) Synthesis of N,N-(diferrocenylmethyl)glycine

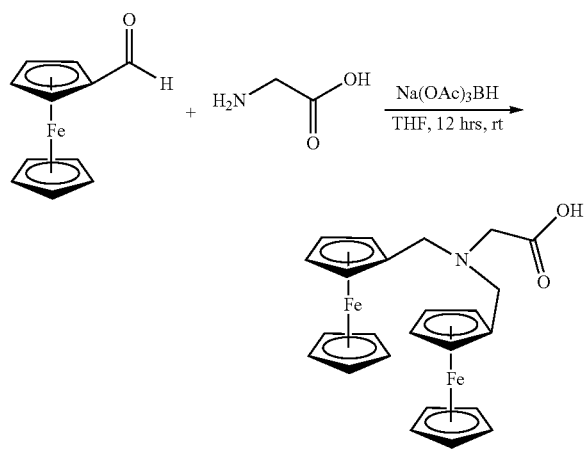

Ferrocene carboboxaldehyde (2.1 g) was added to a round bottomed flask containing dry THF (20 mL). Glycine (0.5 g) was added to the solution and the reaction was stirred under $N_2$. Sodium triacetoxyborohydride (2.3 g) was added portionwise to the stirring solution. The reaction was stirred over night. The solution was then partitioned between ethyl acetate (40 mL) and 1M aqueous sodium hydroxide (40 mL). The organic fraction was washed with saturated aqueous $NaHCO_3$ (sat; 20 mL), brine (40 mL) and water (40 mL). The organic fraction was dried using $MgSO_4$ and the solvent was removed. The crude product was then columned (solvent A: petroleum ether 40-60:TEA 95:5, Solvent B: ethyl acetate:TEA 95:5). The product was an dark orange solid (80%). $^1$H NMR (250 MHz, $CDCl_3$) δ 4.099 (1H, s, CpH), 4.052 (1H, s, CpH), 4.022 (7H, s, FcCpH), 3.549 (4H, t, J=6.75, 2×$CH_2$), 3.348 (2H, s, $CH_2$), 1.979 (1H, s, OH). $^{13}$C NMR (75.5 Hz, $CDCl_3$) δ 171.5, 78.0, 77.5, 77.1, 68.9, 67.4, 61.1. HRMS (ESI) calcd for $C_{24}H_{25}N_1O_2Fe_2$ m/z: 477.3974 found 477.4213

(b) Synthesis of Label C from Diferrocenylglycine

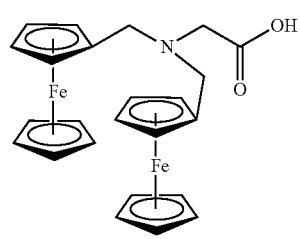

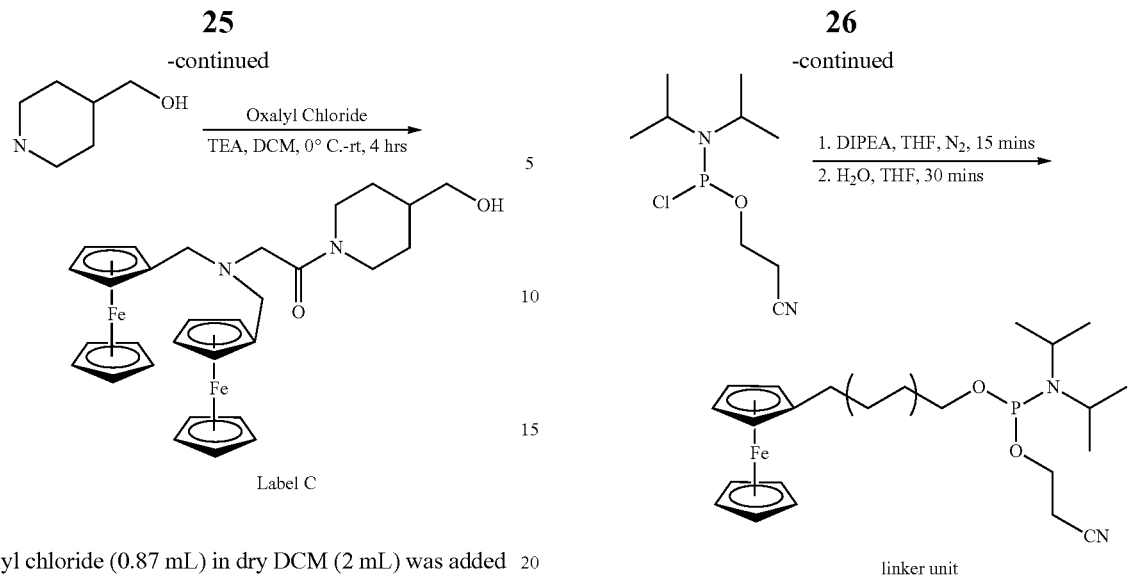

Label C

Oxalyl chloride (0.87 mL) in dry DCM (2 mL) was added dropwise via a pressure equalising dropping funnel to a stirred solution of the di-ferrocenyl glycine derivative obtained in 3(a) above in dry DCM (100 mL) at 0° C. under $N_2$. The reaction warmed to room temperature and stirred for 2 hrs. Then the solvent was removed and the acid chloride product was taken up in dry DCM (75 mL). 6-amino hexan-1-ol (0.56 g) in dry DCM (75 mL) was added dropwise via a dropping funnel at 0° C. under $N_2$. The reaction was then stirred for 2 hrs while warming to room temperature. The solution was then washed with $NaHCO_3$ (sat; 100 mL) and 1.0M HCL (100 mL). The organic fraction was dried over $MgSO_4$ then the solvent was removed to yield the product (85%). An orange/yellow solid. $^1$H NMR (250 MHz, $CDCl_3$) δ 4.11 (12H, s, FcCp), 3.65 (4H, t, J=6.0 Hz, $CH_2$), 3.55 (2H, s, $CH_2$), 1.48-1.18 (5h, m, $CH_2$). $^{13}$C NMR (75.5 Hz, $CDCl_3$) δ 173.32, 77.80, 77.39, 76.90, 62.10, 38.85, 35.45, 32.02, 30.67, 26.75, 25.54, 25.44. m/z: 576.

Figure 4:
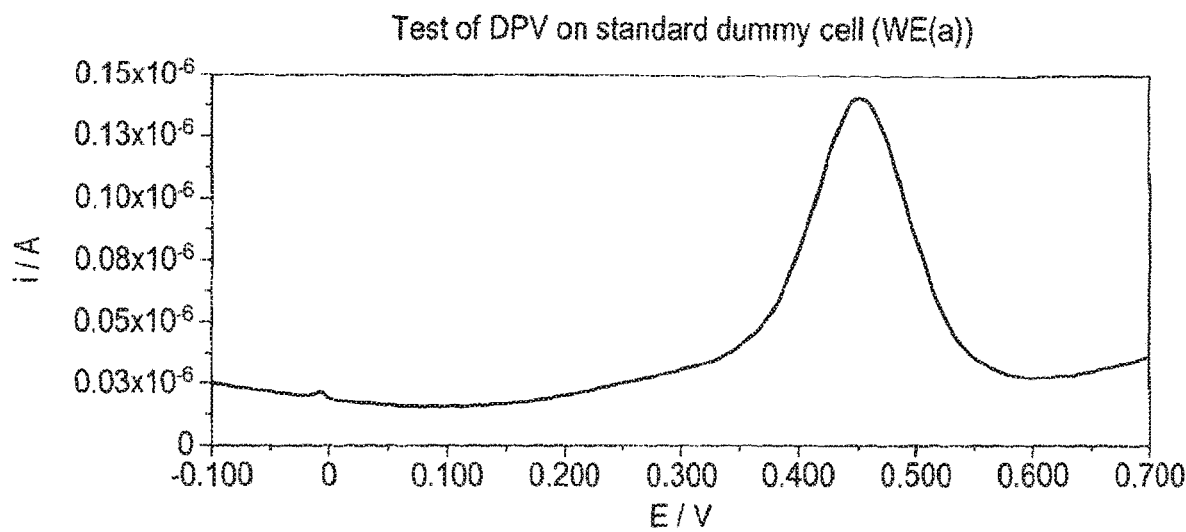
FIG. 4 is a differential pulse voltammogram of Label C as manufactured in Example 3 below.

The electrochemistry of the product compound Label C is shown in Table 3 below and on the voltammogram of FIG. 4

TABLE 3

| Electrochemical activity of Label C | |
|---|---|
| Peak Position (mV) | Peak Height |
| 410 | $6.79e^{-6}$ |
| 425 | $8.47e^{-6}$ |
| 415 | $8.56e^{-6}$ |

Example 4: General Synthetic Procedure for Attaching Phosphoramidite Functional Group

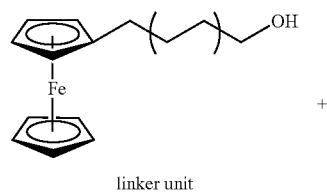

linker unit

+

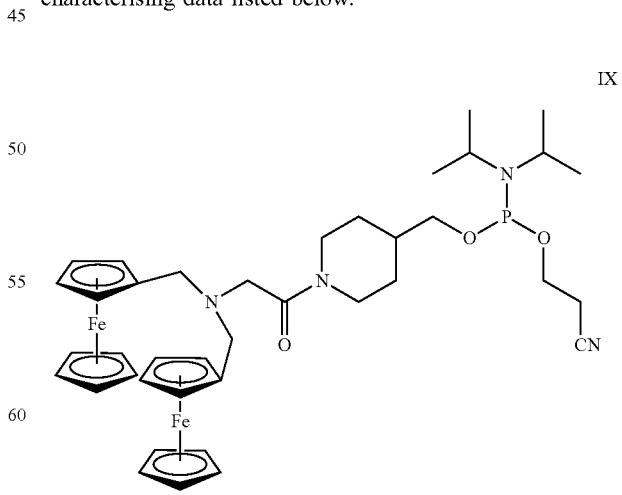

linker unit

The ferrocenyl derivative shown as a starting material in the above reaction scheme is illustrative, and may be replaced by a molar equivalent of any of the compounds made in Examples 1 to 3 above or Examples 9 to 13 below.

N,N-diisopropylethylamine (0.4 mL, 8.4 mmol) was added to a stirred solution of the ferrocene derivative (2.1 mmol) in dry THF (25 mL) under a nitrogen atmosphere. 2-cyanoethyldiisopropylchlorophosphoramidite (0.2 ml, 3.15 mmol) was added dropwise and the resulting mixture was stirred for 15 mins. MilliQ filtered water (200 mL) was added and the solution was stirred for a further 30 mins. Ethyl Acetate-Triethylamine (1:1, 25 mL) was added, a precipitate formed. The mixture was washed with saturated $NaCHCO_3$ (25 mL) and MilliQ filtered water (25 mL). The organic fraction was dried over $MgSO_4$ and the solvent was removed under vacuo. The crude product was then purified by silica gel chromatography (petroleum ether:ethyl acetate 9:1).

Using the above-described process with Label C as the ferrocenyl starting material, a phosphoramidite funtionalised compound of formula IX was obtained, having the characterising data listed below.

IX $^1$H NMR (500 MHZ, $CDCl_3$) δ 4.23 (2H, s, Cp), 4.18 (2H, s, Cp), 4.13 (15H, s, Cp), 3.90-3.82 (2H, m, $CH_2$), 3.71-3.54 (4H, m, $CH_2$), 3.44 (4H, s, $CH_2$), 2.64 (2H, t, J=6, $CH_2$), 2.35 (2H, t, J=6.5, CH$_2$), 1.69-1.35 (85H, m, CH$_2$, CH), 1.23 (12H, t, J=7, CH$_3$). $^{31}$P NMR (DEC) (202.5 Hz, CDCl$_3$) δ 147.23. HRMS (ESI) calculated for C$_{39}$H$_{53}$N$_4$O$_3$Fe$_2$P$_1$ m/z: 768.0973 found 768.1254.

Example 5—Use of Label a Coupled to Oligonucleotide Probe

Synthesis of oligonucleotide was carried out using standard oligonucleotide solid-phase synthesis techniques the nucleotides being added stepwise to the 5' end of the oligonucleotide strand. Each addition to the oligonucleotide chain involves four reactions which are the de-blocking, coupling, capping and oxidation steps. Once the oligonucleotide sequence has been completed to the desired length the electrochemical label was added via a phosphoramidite linkage.

Method

The target sequence was amplified from a *Chlamydia trachomatis* target by a standard PCR method using 5' and 3' target specific primers and a uracil-DNA glycosylase (UDG) Step. PCR conditions are summarised in Table 1 below. When the PCR reaction was complete, a oligonucleotide probe (labelled with electrochemical Label A at the 5' terminal) complementary to a sequence intermediate in position on the target between the 5' and 3' primers was added to the PCR reaction products and allowed to anneal to its target on the amplicon. T7 exonuclease (which is specific for double stranded nucleic acid) was added to the tube and incubated to allow it to digest dsRNA. Probe was digested by the T7 exonuclease to the extent that it was annealed to the PCR amplicon. Electrochemical detection was then carried out, showing a peak at a characteristic redox potential of 0.2V for the digest product nucleotide labelled with Label A.

TABLE 4

| Component | Concentration |
|---|---|
| PCR buffer | 1X |
| MgCl$_2$ | 5 mM |
| dUTP mix | 1X |
| Forward primer | 0.04 μM |
| Reverse primer | 0.3 μM |
| Taq | 2.5 U |
| UNG | 0.5 U |

Figure 5:
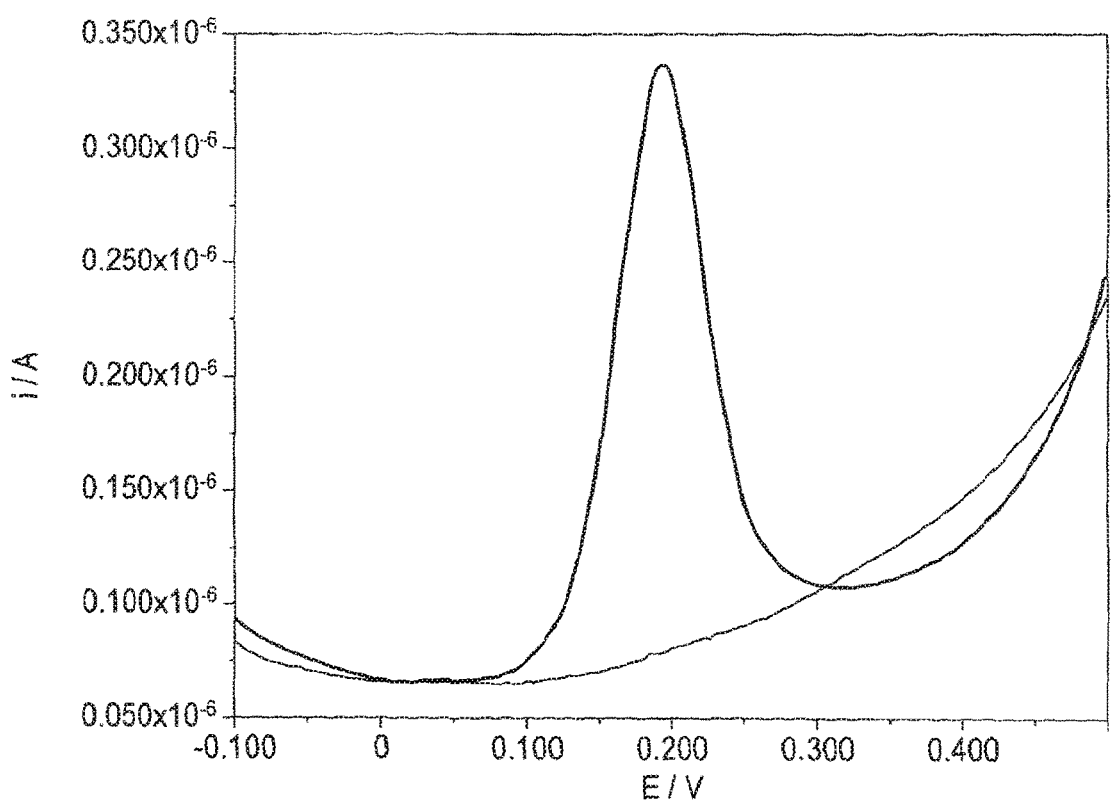
FIG. 5 shows the voltammetric scans for both a *Chlamydia* positive and a negative sample according to Example 5(a) below.

UNG protocol:
37° C.×10 minutes
94° C.×10 minutes
PCR protocol:
94° C.×30 seconds
58° C.×45 seconds
72° C.×60 seconds
Repeat steps×39 cycles (40 cycles in total)
72° C.×7 minutes Results FIG. 5 shows the peak height, as a current, at the known (label specific) redox potential for both a *Chlamydia trachomatis* positive sample (the strong peak) and negative sample (absence of peak).

Figure 6:
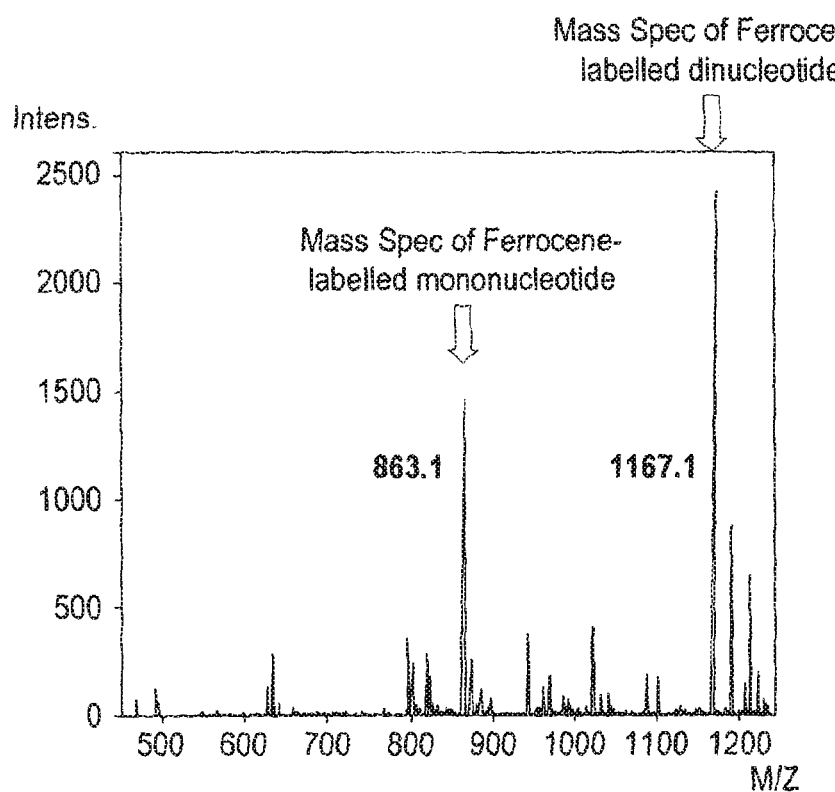
FIG. 6 is a mass spec analysis of a mononucleotide and a dinucleotide synthesised with the label A electrochemical label as described in Example 5(a) below.
Figure 7:
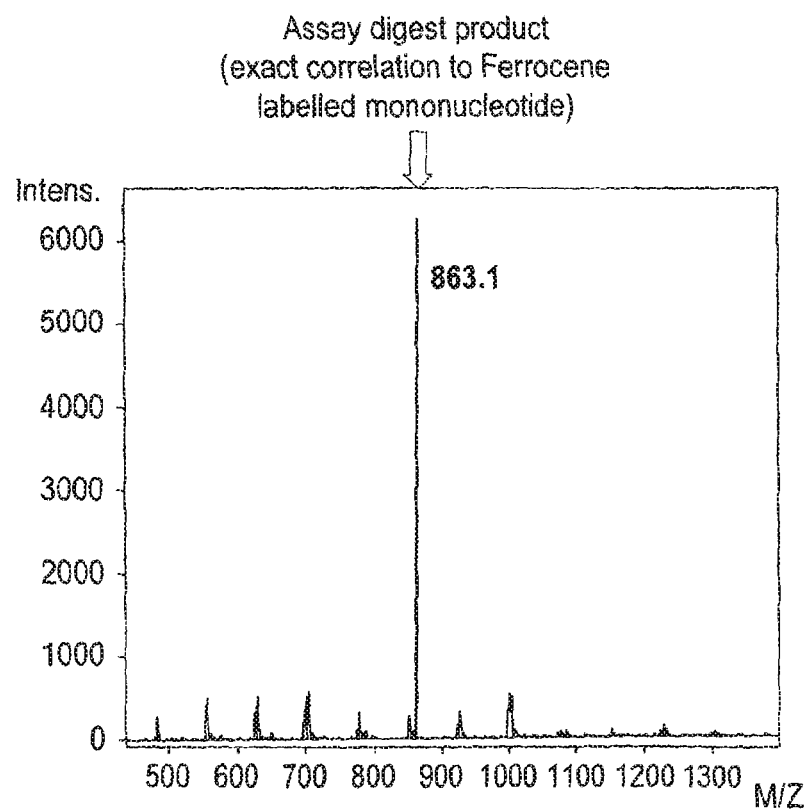
FIG. 7 is a mass spec analysis of the assay product of Example 5(a)

FIG. 6 shows a mass spec analysis of a mononucleotide and a dinucleotide synthesised with the label A electrochemical label. FIG. 7 is a mass spec analysis of the assay product, which shows exact correlation to a mononucleotide coupled to the label A electrochemical label, the electrochemical moiety detected in the assay.

Figure 8:
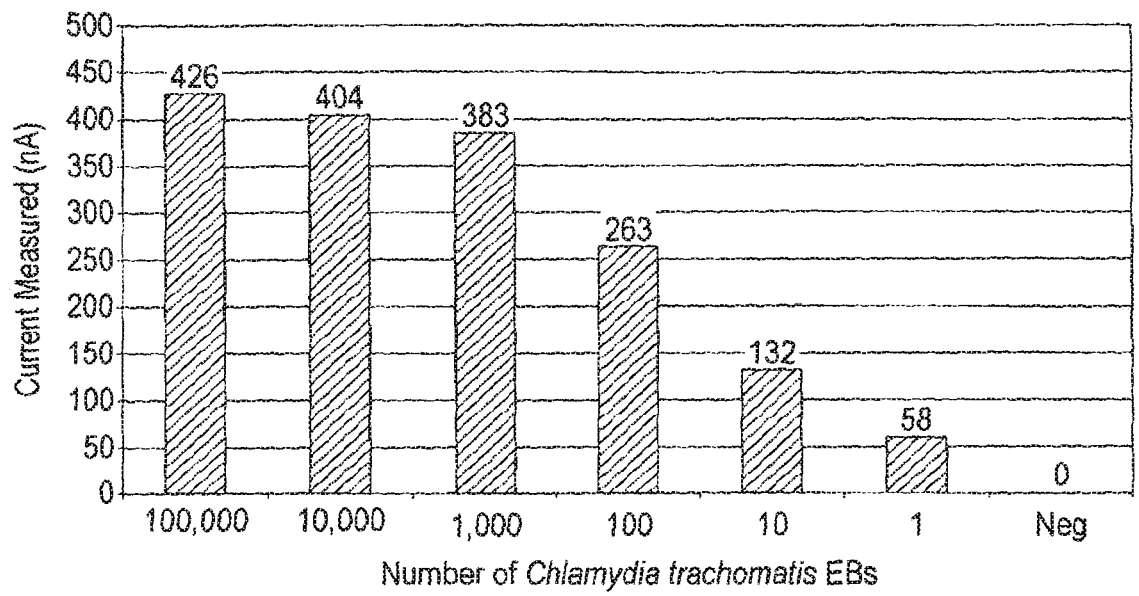
FIG. 8 is a bar graph showing current measurements taken when a *Chlamydia* target is added directly to a PCR reaction at a range of concentrations and detected using a oligonucleotide probe as described in Example 5(b) below.

FIG. 8 shows the results of an experiment where the *Chlamydia* target is added directly to the PCR reaction at a range of concentrations. This is amplified using PCR, then detected using a label A oligonucleotide probe.

Figure 9:
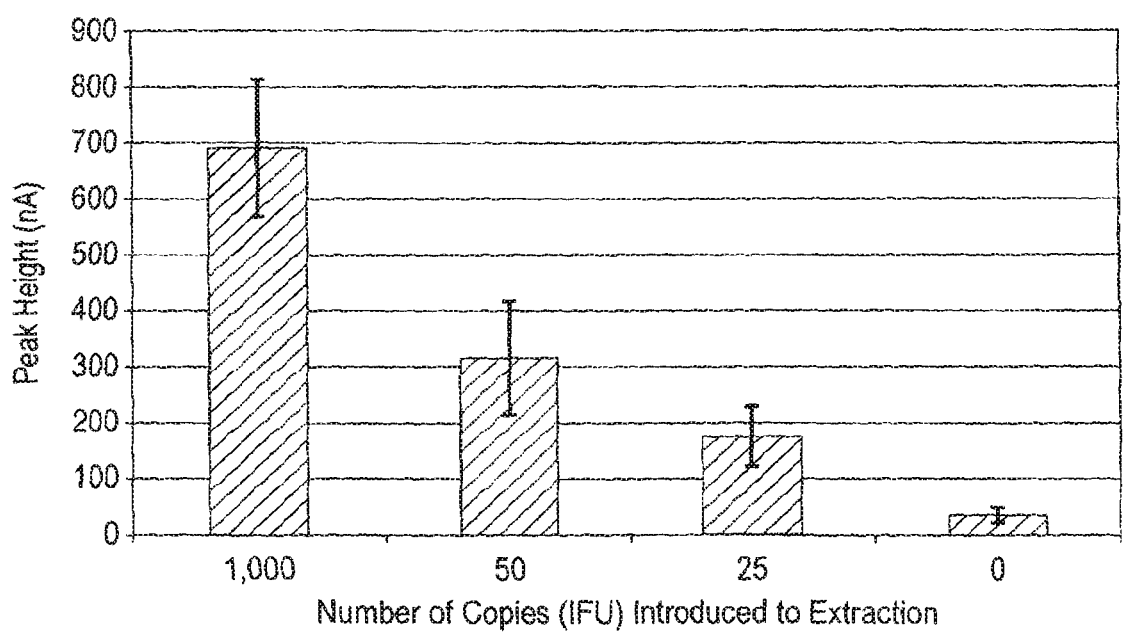
FIG. 9 is a bar graph showing peak current at a range of concentrations when the *Chlamydia* target was added to a DNA extraction process and the output from the extraction process was amplified using PCR, then detected using an oligonucleotide probe labelled with Label A, as described in Example 5(c) below.

FIG. 9 shows the result for an experiment where a range of concentrations of the *Chlamydia* target are added to a DNA extraction process (i.e. not added directly to the PCR) and the output from the extraction process is amplified using PCR, then detected using an oligonucleotide probe labelled with Label A.

Figure 10:
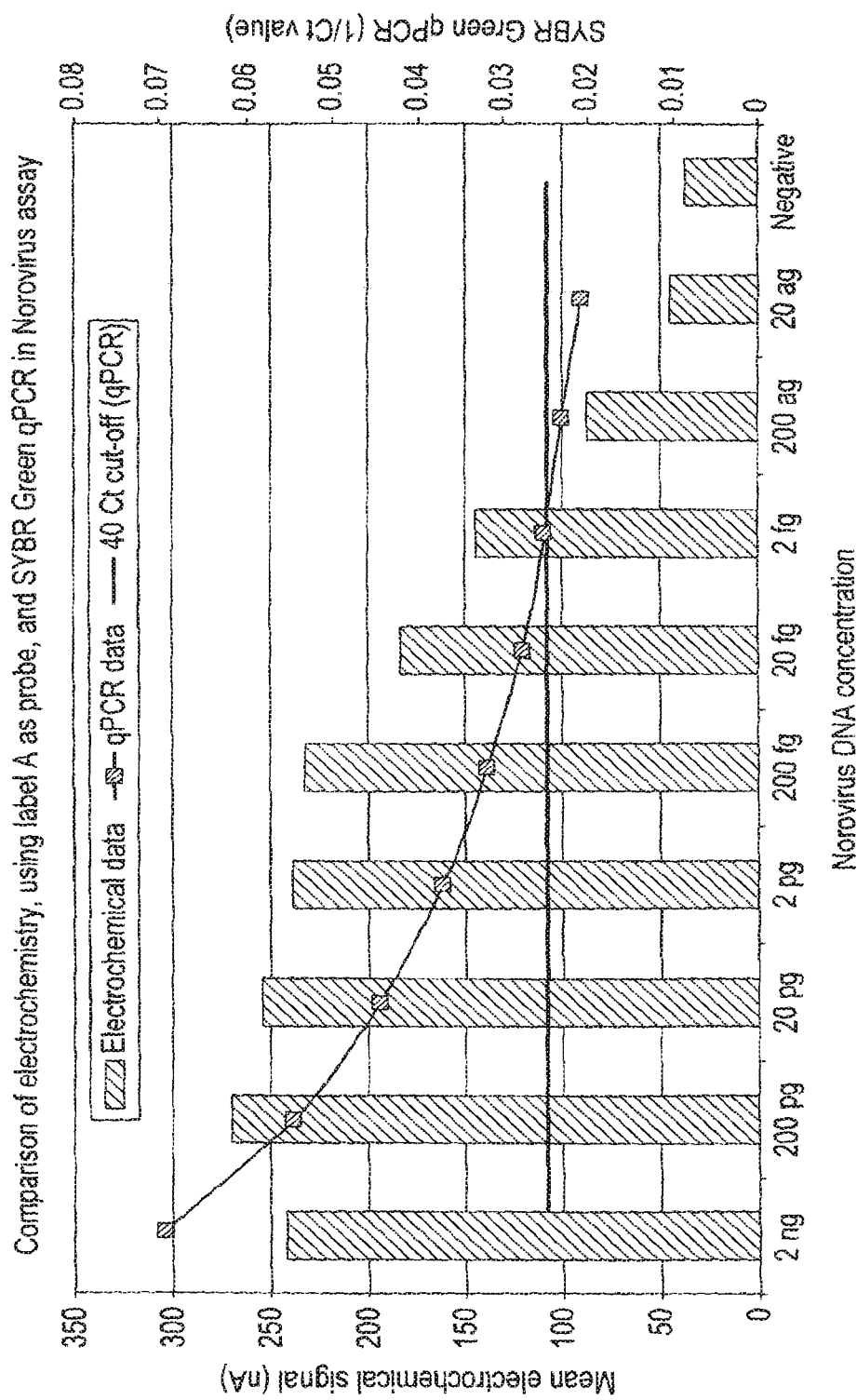
FIG. 10 shows a comparison between electrochemical detection using the label A probe and a SYBR Green based qPCR assay for Norovirus.

Example 6—Comparison of Performance to qPCR a) FIG. 10 shows a comparison between electrochemical detection using the label A probe and a SYBR Green based qPCR assay for Norovirus. The materials and protocols are as follows:

Bioline SensiMix dU
Bioline 1×SYBR Green
0.3 μM forward primer
0.3 μM reverse primer
0.5 U UNG
UNG protocol:
37° C.×10 minutes
60° C.×2 minutes
qPCR protocol:
95° C.×10 minutes (taq activation step)
95° C.×15 seconds
45° C.×10 seconds
72° C.×10 seconds (SYBR acquisition)
Repeat last 3 steps×39 cycles (40 cycles in total)
47° C.-95° C. in 1° C. increments (end-point melt to check for non-specific amplification)

A decimalised inverse of the Ct value has been used for the qPCR results to provide a direct comparison to the electrochemical results.

Figure 11:
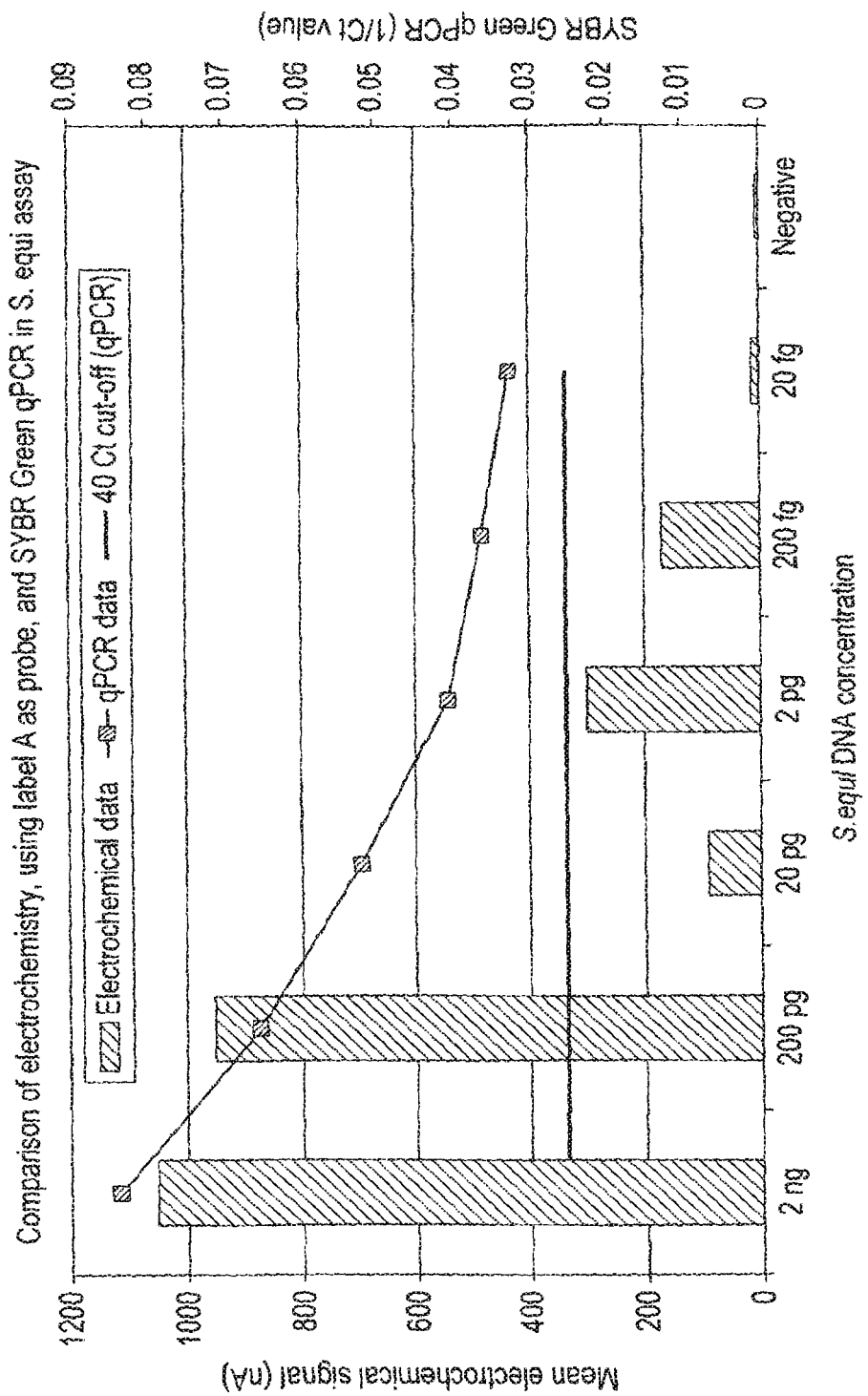
FIG. 11 shows a comparison between electrochemical detection using the label A probe and a SYBR Green based qPCR assay for *Streptococcus equi;*

The data shows the limit of detection for the electrochemical assay to be 200 ag. The limit of detection for the qPCR assay is shown as between 2 and 20 fg. Below this level the Ct value is greater than 40-cycle cut-off, shown by the horizontal line as the inverse of a Ct value of 40. The qPCR negatives did not rise above the threshold. This demonstrates the advantageous sensitivity of the electrochemical assay using label A.

b) FIG. 11 shows a comparison between electrochemical detection using the label A probe and a SYBR Green based qPCR assay for *Streptococcus equi*.

The data shows that both the electrochemical assay and the qPCR assay are capable of detecting down to the lowest DNA concentration tested in this experiment (20 fg). The signal:noise ratio for the electrochemical detection at 20 fg was 4:1 in this experiment. 20 fg equates to 8 genomic copies of *S. equi* DNA.

Example 7—Label a Directly Bound to Protein a) FIG. 12*a* is a voltammetric scan using label A coupled directly to the primary amine of a commercially available anti-goat IgG, using an active NHS ester (N-hydroxysuccinimide ester).

The following generalised reaction scheme illustrates attachment of the label to a free amine of, for example, a lysine residue in the anti-goat IgG.

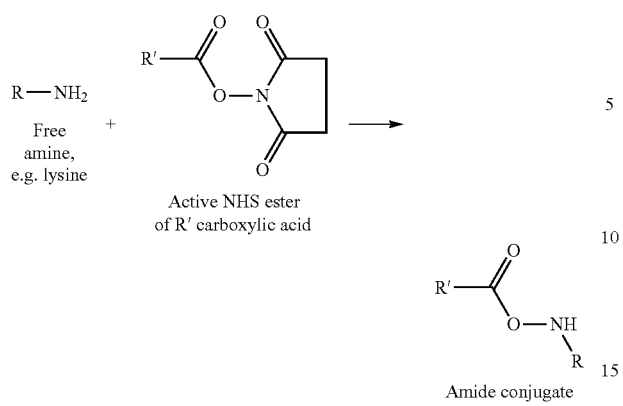

Commercially available biotinylated goat IgG was immobilised onto a streptavidin coated microtitre well. The label A anti-goat IgG was then incubated in the well containing the immobilised goat IgG, this was then removed with washing. A papain solution was added to the well and incubated to allow digestion of the secondary antibody, with the resulting solution read electrochemically. The control in this experiment followed the same procedure, but the final incubation was carried out in buffer only, without papain.

FIG. 12a shows that an electrochemical signal at the known oxidation potential for the label A is released when papain is present, but is not present in the absence of papain. This shows that the label A is directly bound to the antibody in this assay and signal is only observed when this antibody is digested, releasing the electrochemical label.

b) The data in FIG. 12b uses the same model assay as in Example 7a) above, except that a papain digestion time course experiment is shown. In this experiment the control was the label A secondary antibody (anti-goat IgG) which was added to a well with no immobilised goat IgG antibody.

Example 8—Label A Bound to Microparticles

A biotin molecule was coupled to label A. The biotinylation can be carried out in an automated oligonucleotide synthesiser or using standard laboratory conditions by reaction of ferrocenyl phosphoramidite label with N-hydroxysuccinimide (NHS) esters of biotin.

Paramagnetic treptavidin particles were washed ×3 (phosphate buffer) and mixed with biotinylated label, followed by incubation for 1 hour at room temperature with mixing. The particles were washed ×2 (phosphate buffer) and washed ×1 (PCR buffer) They were resuspended in final buffer (PCR buffer)

Following each wash step the supernatants were tested for electrochemical signal, and if necessary washing was repeated until the supernatants showed no indication of free electrochemical label.

These particles were assayed at a range of concentrations to validate that the observed electrochemical signal was attributable to label A coupled to the magnetic particles. This involved magnetic capture of the particles and resuspension in a range of buffer volumes. The results are shown in FIG. 13.

Example 9—Synthesis of (N,N-diferrocenylmethyl-2-aminoethoxy) ethanol (Label D)

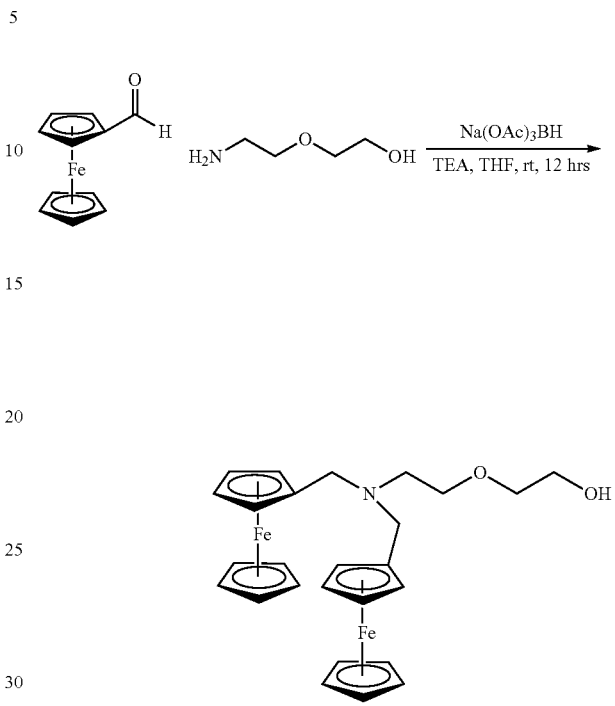

Ferrocene carboxaldehyde (2.1 g, 9.81 mmol) and (aminoethoxy) ethanol (0.5 g, 4.27 mmol) in dry THF (25 mL) were added to an oven dried flask. Sodium triacetoxyborohydride (2.3 g, 10.90 mmol) was added portionwise to the solution. The reaction was left overnight. The reaction was taken up in ethyl acetate (40 mL), the organic layer was washed with $NaCO_3$ (sat; 20 mL), Brine (20 mL) and MilliQ water (20 mL). The organic fraction was then dried over magnesium sulfate and the solvent removed in vacuo. The crude product is then columned using 9:1 solution B: solution A (solution A: ethyl acetate 95% TEA 5%, solution B: Petroleum ether 40-60 95%, TEA 5%) to elicit the pure product label D (dark orange solid). 85% Yield $^1$H NMR (300 MHz, $CDCl_3$) δ 4.18 (2H, s, Cp), 4.17 (2H, s, Cp), 4.13 (15H, s, Cp), 3.66 (4H, t, J=6.25 Hz, $CH_2$), 3.48 (2H, s, $CH_2$), 2.20 (2H, t, J=6, $CH_2$). $^{13}$C NMR (75.5 Hz, $CDCl_3$) δ 77.83, 77.40, 76.98, 70.58, 68.88, 63.36, 53.02, 52.17, 33.10, 27.43, 25.88. HRMS (ESI) calculated for $C_{26}H_{33}N_1O_2Fe_2$ m/z 501.1430 found 501.1438.

The electrochemistry of Label D is shown in the table below and on the voltammogram in FIG. 14:

TABLE 5

| Electrochemical activity of Label D | |
|---|---|
| Peak Position (mV) | Peak Height |
| 242 | $9.31e^{-6}$ |
| 245 | $9.38e^{-6}$ |
| 239 | $9.76e^{-6}$ |

Example 10—Synthesis of di-ferrocenyl glycine amino alcohol N,N-2-(diferrocenylmethylamino) acetyl-6-aminohexanol also named N-(6-hydroxyl-hexyl)-2-((diferrocenylmethyl) amino)-acetamide (Label E)

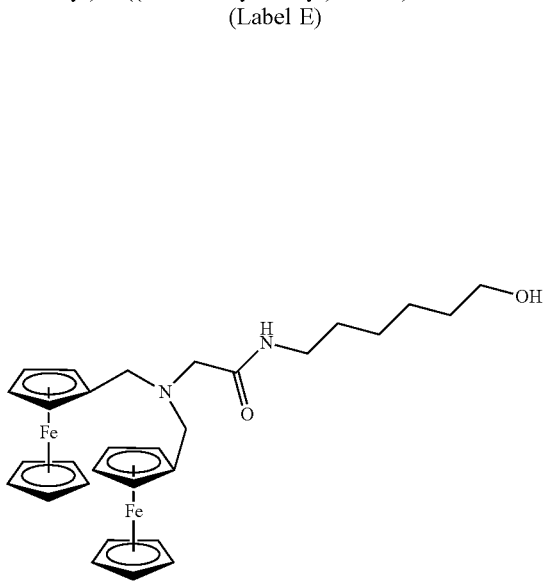

Oxalyl chloride (0.87 mL) in dry DCM (2 mL) was added dropwise via a pressure equalising dropping funnel to a stirred solution of di-ferrocenyl glycine (obtained as described in Example 3a) in dry DCM (100 mL) at 0° C. under $N_2$. The reaction warmed to room temperature and was stirred for 2 hrs. Then the solvent was removed and the acid chloride product was taken up in dry DCM (75 mL). 6-aminohexan-1-ol (0.56 g) in dry DCM (75 mL) was added dropwise via a dropping funnel at 0° C. under $N_2$. The reaction was then stirred for 2 hrs while warming to room temperature. The solution was then washed with $NaHCO_3$ (sat; 100 mL) and 1.0M HCL (100 mL). The organic fraction was dried over $MgSO_4$ then the solvent was removed to yield the product Label E (85%). An orange/yellow solid. $^1$H NMR (250 MHz, $CDCl_3$) δ 4.11 (12H, s, FcCp), 3.55 (4H, t, J=6.0 Hz, $CH_2$), 3.31 (2H, s, $CH_2$), 1.48-1.18 (12h, m, $CH_2$). $^{13}$C NMR (75.5 Hz, $CDCl_3$) δ 173.32, 77.80, 77.39, 76.90, 62.10, 38.85, 35.45, 32.02, 30.67, 26.75, 25.54, 25.44. HRMS (ESI) calculated for $C_{24}H_{25}N_1O_2Fe_2$ m/z: 576.0988 found 576.1264.

The electrochemistry of Label E is illustrated in the data in the table below.

TABLE 6

| Electrochemical activity of Label E | |
|---|---|
| Peak Position | Peak Height |
| 504 | $6.61e^{-6}$ |
| 506 | $5.51e^{-6}$ |
| 507 | $3.28e^{-6}$ |

Example 11—6-(bis((1'-vinylferrocenyl)1-methyl-ferrocenyl)amino)hexan-1-ol

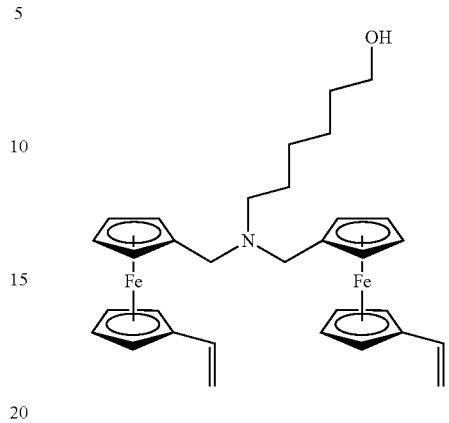

1'-Vinyl ferrocene carboxaldehyde (122 mg, 0.5 mmol) was dissolved in dry THF (5 cm$^3$) and treated with 6-aminohexan-1-ol (29 mg, 0.25 mmol) and sodiumtrisacetoxyborohydride (205 mg, 1.25 mmol) successively. The solution was allowed to stir at room temperature overnight. After this time the reaction was quenched by addition of 10 cm$^3$ saturated $NaHCO_3$. The organic layer was separated, then the aqueous layer back extracted with ethyl acetate (3×10 cm$^3$). Combined organic extracts were dried over magnesium sulfate, filtered then concentrated in vacuo to give a red solid. The product was purified by silica chromatography, eluting with 1:1 (ethyl acetate:hexane)+1% ammonium hydroxide to give the desired product as an orange oil 72 mg, in 50% yield.

$^1$H NMR (500 Mhz; $CDCl_3$) $δ_H$ 6.38 (2H, dd, J 17.6, 10.7 =CH), 5.30 (2H, dd, J 10.7, 1.5, =$CH_2$), 5.03 (2H, dd, J 10.7, 1.5, =$CH_2$), 4.25 (4H, t, J 1.8, CpH), 4.15 (4H, t, J 1.8, CpH), 4.07 (8H, s, CpH), 3.59 (2H, t, J 6.6, $OCH_2$), 3.32 (4H, s, 2×$F_cCH_2$), 2.23, (2H, app t, J 7.4, $NCH_2$), 1.49-1.55 (2H, m, $CH_2$), 1.33-1.39 (2H, m, $CH_2$), 1.22-1.33 (4H, m, $CH_2$); $^{13}$C NMR (125 Mhz; $CDCl_3$) $δ_c$ 134.3, 111.3, 83.7, 83.6, 71.4, 69.2, 69.0, 67.2, 62.8, 52.1, 32.7, 27.1, 25.5; HRMS, m/z (ESI) 566.1825 (1.8%, [M+H], $C_{32}H_{39}Fe_2NO$ requires 566.1808); Electrode Potential: 298 mV.

Example 12: 6-(bis((1'-bromoferrocenyl)$_1$-methyl-ferrocenyl)amino)hexan-1-ol

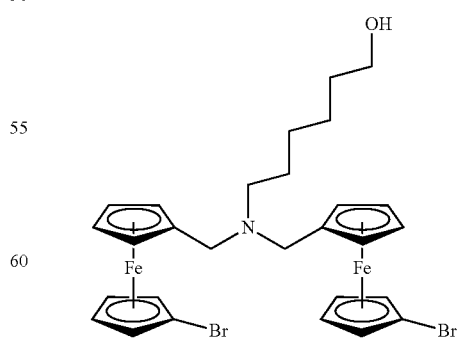

1'-Bromo ferrocene carboxaldehyde (85 mg, 0.29 mmol) was dissolved in dry THF (3 cm$^3$) and treated with 6-aminohexan-1-ol (25 mg, 0.144 mmol) and sodiumtrisacetoxyborohydride (59.3 mg, 0.36 mmol) successively. The solution was allowed to stir at room temperature overnight. After this time the reaction was quenched by addition of 5 cm$^3$ saturated NaHCO$_3$. The organic layer was separated, then the aqueous layer back extracted with ethyl acetate (3×10 cm$^3$). Combined organic extracts were dried over magnesium sulfate, filtered then concentrated in vacuo to give a red solid. The product was purified by silica chromatography, eluting with 1:1 (ethyl acetate:hexane)+1% ammonium hydroxide to give the desired product as an yellow oil 17 mg, in 17% yield.

$^1$H NMR (500 Mhz; CDCl$_3$) $\delta_H$ 4.32, (4H, t, J 1.8, F$_c$H), 4.21 (8H, s, F$_c$H), 4.05 (4H, t, J 1.8, F$_c$H), 3.63 (2H, t, J 6.5, OCH$_2$), 3.46 (4H, s, F$_c$CH$_2$N), 2.31 (2H, t, J 7.1, NCH$_2$), 1.45-1.58 (4H, m, CH$_2$), 1.27-1.36 (4H, m, CH$_2$); $^{13}$C NMR (125 Mhz; CDCl$_3$) $\delta_c$ 78.4, 72.9, 70.8, 70.5, 68.6, 67.9, 63.1, 62.8, 52.1, 33.0, 27.3, 26.0; HRMS, m/z (ESI) 669.7929 (2.7%, [M+H], C$_{28}$H$_{34}$Fe$_2$Br$_2$NO requires 669.9705); Electrode Potential: 437 mV.

Example 13:
6-(bis((2-methylferrocenyl)methyl)amino)hexan-1-ol

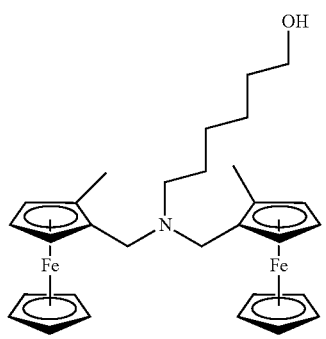

Methylferrocenecarboxaldehyde (1 g, 5 mmol) was dissolved in dry THF (30 cm$^3$). 6-aminohexan-1-ol (0.25 g, 2.13 mmol) was added. Then sodium triacetoxyborohydride (1.3 g, 6.16 mmol) was added to the reaction mixture. The solution was stirred under nitrogen at room temperature overnight. Ethyl acetate (20 cm$^3$) and 1M NaOH (20 cm$^3$) were then added and the organic layer was then extracted with saturated NaHCO$_3$ (25 cm$^3$), brine (25 cm$^3$) and Milli Q filtered water (25 cm$^3$) then dried over magnesium sulfate and the solvent removed in vacuo to yield an orange oil. The crude product is then columned using 9:1 solution B: solution A (solution A: ethyl acetate 95% TEA 5%, solution B: petroleum ether 40-60 95%, TEA 5%) to elicit the pure product (orange oil). (0.95, 65%). $^1$H NMR (300 MHz; CDCl$_3$) $\delta_H$ 4.18 (2H, s, CpH), 4.17 (2H, s, CpH), 4.13 (15H, s, CpH), 3.66 (4H, t, J 6.25, CH$_2$), 3.48 (2H, s, CH$_2$), 2.36 (3H, s, CH$_3$), 2.20 (2H, t, J 6.1, CH$_2$), 1.59-1.31 (6H, m, CH$_2$). $^{13}$C NMR (75.5 Hz; CDCl$_3$) $\delta_c$ 77.8, 77.4, 76.9, 70.5, 68.9, 63.3, 53.0, 52.1, 33.1, 27.4, 25.8, 12.4; HRMS, m/z (ESI) 539.8156 (10%, [M+H], C$_{30}$H$_{47}$N$_1$O$_1$Fe$_2$ requires 539.8232); Electrode potential: 330 mV.

TABLE 7

| Effect on electrode potential of substituents on ferrocenyl moieties of Label A ||| |
|---|---|---|
| Example | Fc substituent | Electrode potential |
| 1 | None | 275 mV |
| 2 | Dimethylaminomethyl | 380 mV |
| 11 | 1'-vinyl | 298 mV |
| 12 | 1'-bromo | 437 mV |
| 13 | 2-methyl | 330 mV |

The data in the above table illustrates how inclusion of a substituent on the ferrocenyl moieties and the selection of that substituent may be used to influence the electrode potential. This enables the electrochemical detection of compounds to be carried out under a variety of different conditions, for example selecting an optimum measurement potential or avoiding conditions under which measuring sensitivity may be compromised by interference with impurities that may be present. Furthermore, the use of labels with different electrode potentials allows for the development of multiplex reactions, in which more than one determination can be carried out in the same sample.

What is claimed is:

1. A method of detecting a nucleic acid, the method comprising:
    contacting the nucleic acid with a complementary nucleic acid probe under conditions to allow hybridization between said probe and an amplicon; and
    selectively degrading the probe, wherein the probe is labelled with the compound:

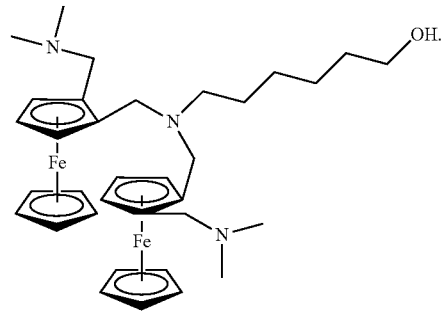

2. The method of claim 1, further comprising measuring electrochemical activity of the compound labelling the probe, wherein said electrochemical activity is dependent either quantitatively or qualitatively on the degradation of the probe.

* * * * *